(12) United States Patent
Heidecker et al.

(10) Patent No.: US 6,897,288 B1
(45) Date of Patent: May 24, 2005

(54) MAGE-A12 ANTIGENIC PEPTIDES AND USES THEREOF

(75) Inventors: Leonora Heidecker, Brussels (BE); Benoit van den Eynde, Rixensart (BE); Thierry Boon-Falleur, Brussels (BE); Francis Brasseur, Brussels (BE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/692,401

(22) Filed: Oct. 19, 2000

Related U.S. Application Data

(60) Provisional application No. 60/179,570, filed on Feb. 1, 2000, and provisional application No. 60/160,374, filed on Oct. 19, 1999.

(51) Int. Cl.$^7$ .......................... C07K 7/06; A61K 39/00
(52) U.S. Cl. .................. 530/328; 424/185.1; 424/277.1
(58) Field of Search ....................... 530/328; 424/185.1, 424/277.1, 278.1

(56) References Cited

U.S. PATENT DOCUMENTS

| | | | |
|---|---|---|---|
| 5,342,774 A | | 8/1994 | Boon et al. |
| 5,662,907 A | * | 9/1997 | Kubo et al. |
| 5,846,827 A | * | 12/1998 | Celis et al. |

FOREIGN PATENT DOCUMENTS

| | | |
|---|---|---|
| WO | WO 95/25740 A1 | 9/1995 |
| WO | WO 97/31017 A1 | 8/1997 |
| WO | WO 99/14326 A1 | 3/1999 |

OTHER PUBLICATIONS

PIR_68 Accession No. 154519, 1996.*
Rammensee et al. Immunogenetics 41: 178–228, 1995.*
Ngo et al. The Protein Folding Problem and Tertiary Structure Prediction. K. Merz and S. Le Grand, Eds. Birkhauser Boston, 1994, pp. 491–495.*
Guo et al. Nature. 360: 364–366, 1992.*
Englehard, V.H. Curr Opin Immunol. 6: 13–23, 1994.*
Smilek, DE et al. Proc. Nat. Acad. Sci. (USA) (Nov. 1991) 88:9633–9637.*
Heidecker et al., *J. Immunol.* 164: 6041–6045 (2000).
Lally et al., *FASEB J.* 14(6): A1005–Abstr. (2000).
Traversari et al., *J. Exp. Med.* 176:1453–1457, 1992.
Van der Bruggen et al., *Science* 25: 1643–1647, 1991.
De Plaen et al., *Immunogenetics* 40:360–369, 1994.
De Smet et al., *Immunogentics* 39(2):121–129, 1994.
De Smet et al., GenBank Accession No. L18877, locus HUMMAGE12X.
Panelli et al., *J. Immunol* 164(8):4382–4392, 2000.

* cited by examiner

*Primary Examiner*—Christina Chan
*Assistant Examiner*—F. Pierre VanderVegt
(74) *Attorney, Agent, or Firm*—Wolf, Greenfield & Sacks, P.C.

(57) ABSTRACT

The invention provides antigenic peptides derived from MAGE-A12 polypeptides and presented by HLA molecules. Methods for diagnosis and treatment which involve the polypeptides also are provided.

16 Claims, 4 Drawing Sheets

SEQUENCE LISTING

<160> NUMBER OF SEQ ID NOS: 56

<210> SEQ ID NO 1
<211> LENGTH: 4523
<212> TYPE: DNA
<213> ORGANISM: Homo sapiens
<220> FEATURE:
<221> NAME/KEY: CDS
<222> LOCATION: (2960)...(3904)

<400> SEQUENCE: 1
tggcctggga cccgcagcca ttctctacaa ggggtgcagc tgtgcaaatg cacagacgtt      60
acagaaacag agtatctcct gccaatcact tcatccaaca gccaggagtg aggaagagga     120
ccctcttgag tgaggactga gggtccaccc tcccccacgt agtgaccaca gaatccagct     180
cagtccctct tgtcagccct gctaaactta ggcaataatg tcacccgac cgcacccctc     240 ccccagtgcc acttcagggg gactcagagt cagagacttg gtctgagggg agcagacaca     300
atcggcagag gatggcggtc caggctcagc ctggcatcca agtcaggacc ttgagggatg     360

-continued

```
accaaaggcc cctcccaccc caactcccc caaccccacc aggatctaca gcctcatgat      420
ccccgtccct atccctaccc ctaccccaa caccatcttc atcgttacct ccacctccat      480
ctggatcccc atccaggaag aatccagttc caccctgct gtgaacccag ggaagtcacg      540
gggccggatg tgacgccact gacttgcgcg ttggaggtca gagaacagcg agattctcgc    600
cctgagcaac ggcctgacgt cggcggaggg aagcaggcgc aggctccgtg aggaggcaag    660
gtaagatgcc gagggaggac tgaggcgggc ctcaccccag acagagggcc cccaataatc    720
cagcgctgcc tctgctgcca ggcctggacc accctgcagg ggaagacttc tcaggctcag    780
tcgccaccac ctcaccccgc cacccccgc cgctttaacc gcaggaact ctggtgtaag      840 agctttgtgt gaccagggca gggctggtta gaagtgctca gggcccagac tcagccagga    900
atcaaggtca ggaccccaag aggggactga gggtaacccc cccgcacccc caccaccatt    960 cccatcccccaacaccaacc ccaccccat cccaacac caaacccacc accatcgctc        1020
aaacatcaac ggcaccccca aacccgatt cccatcccca cccatcctgg cagaatcgga    1080
gctttgcccc tgcaatcaac ccacggaagc tccgggaatg gcggccaagc acgcggatcc    1140
tgacgttcac atctgtggct cagggaggga aggggtcgg tatcgtgagt acggcctttg    1200
ggaagcagag gatgggccca agccctcct ggaagataat ggagtccgga gggctcccag    1260
catgccagga caggggccca aagtacccct gtctcaaact gagccacctt ttcattcggc    1320
cgcgggaatc ctagggatac agaccacctt cagcagggag ttggagccca gccctgcgag    1380
gagtcaaggg gaggaagaag agggaggact gaggggacct tggagtccag atcagtggca    1440
accttgggct gggggatcct gggcacagtg gcctaatgtg ccccatgctc attgcgactt    1500
cagggtgaca gatttgcggg ctgtggtctg aggagtggca cttcaggtca gcagagggag    1560
gaatcccagg atctgccgga cccaaggtgt gccccttta tgaggactgg ggatacccc    1620 ggcccagaaa gaagggatgc cacagagtct ggctgtccct tattcttagc tctaagggaa    1680
ccggatcaga gatagctcca attggcaatc tcatttgtac cacaggcagg aggttgggga    1740
accctcaggg agataaggtg ttggtgtaaa gaggagctgt ctgctcattt caggggttg    1800 ggggttgagg aagggcagtc cccggcagga gtaaagatga gtaacccaca ggaggccatc    1860
agaagcctca ccctagaacc aaaggggtca gccctggaca acctacctgg gagtgacagg    1920
atgtggctcc tcctcacttc tgtttccaga tctcagggag ttgaggtcct tttcttcaga    1980
gggtgactca ggtcaacaca ggggccccca tgtagtcgac agacacagtg gtcctaagat    2040
ctaccaagca tccaggtgag aagcctgagg taggattgag ggtaccctg ggccagaacg     2100 ctgacagagg gccccacaga aatctgccct gccctgcta ttccctcaga gagcctgggg    2160
caaggctacc tgctgaggtc cctccattat cctgggatct ttgatgtcag ggaaagggag    2220
gccttggtct gaagggctg cactcaggtc actagacgga ggttctcagg ccctagcagg    2280
agtagtggtg aggaccaagc aggctcgtca cccaggacac ctggactcca atgaatttgg    2340
acatctctca ttgtcctttg tgggaggatc tggttatgta tggccagatg ttggtcccct    2400
catatccttc tgtaccgtat cagggatgtg aattcttgcc atgagagttt ctttggccag    2460
caaaagggcg gtattaggcc ctgcaaggag aaaggtgagg gccctgagtg agcacagaag    2520
gaccctccac cccagtagag tggggacctc acagagtctg gccgaccctc ctgacaattt    2580
tgggaatctg tggctgtact tgcagtctgc accctgaggc ccatggattc ctctcctagg    2640
aatcaggagt tccaagaaca aggcagtgag gccttggtct gaggcagtgt cctgaggtca    2700
cagagcagag ggggtgcaga cagtgccaac actgaaggtt tgccttgaat gcacaccaag    2760
```

-continued

```
cgcaccggcc ccagaacaca tggactccag agggcctggc ctcaccctcc ctactgtcat    2820
tccttcagcc tcagcatgtg ctggccggct gtaccctgag gcgccctctc acttgttcct    2880
tcaggttctg aggagacagg ccccggagca gcactagctc ctgccacac  tcctacctgc    2940 tgccctgacc agagtcatc atg cca ctt gag cag agg agt cag cac tgc aag     2992
                     Met Pro Leu Glu Gln Arg Ser Gln His Cys Lys
                       1               5                      10 cct gag gaa ggc ctt gag gcc caa gga gag gcc ctg ggc ttg gtg ggt      3040
Pro Glu Glu Gly Leu Glu Ala Gln Gly Glu Ala Leu Gly Leu Val Gly
             15                  20                  25 gcg cag gct cct gct act gag gag cag gag act gcc tcc tcc tcc tct      3088
Ala Gln Ala Pro Ala Thr Glu Glu Gln Glu Thr Ala Ser Ser Ser Ser
         30                  35                  40 act cta gtg gaa gtc acc ctg cgg gag gtg cct gct gcc gag tca cca      3136
Thr Leu Val Glu Val Thr Leu Arg Glu Val Pro Ala Ala Glu Ser Pro
     45                  50                  55 agt cct ccc cac agt cct cag gga gcc tcc acc ctc ccc act acc atc      3184
Ser Pro Pro His Ser Pro Gln Gly Ala Ser Thr Leu Pro Thr Thr Ile
 60                  65                  70                  75 aac tat act ctc tgg agt caa tcc gat gag ggc tcc agc aac gaa gaa      3232
Asn Tyr Thr Leu Trp Ser Gln Ser Asp Glu Gly Ser Ser Asn Glu Glu
                 80                  85                  90 cag gaa ggg cca agc acc ttt cct gac ctg gag acg agc ttc caa gta      3280
Gln Glu Gly Pro Ser Thr Phe Pro Asp Leu Glu Thr Ser Phe Gln Val
             95                 100                 105 gca ctc agt agg aag atg gct gag ttg gtt cat ttt ctg ctc ctc aag      3328
Ala Leu Ser Arg Lys Met Ala Glu Leu Val His Phe Leu Leu Leu Lys
        110                 115                 120 tat cga gcc agg gag cca ttc aca aag gca gaa atg ctg ggg agt gtc      3376
Tyr Arg Ala Arg Glu Pro Phe Thr Lys Ala Glu Met Leu Gly Ser Val
    125                 130                 135 atc aga aat ttc cag gac ttc ttt cct gtg atc ttc agc aaa gcc tcc      3424
Ile Arg Asn Phe Gln Asp Phe Phe Pro Val Ile Phe Ser Lys Ala Ser
140                 145                 150                 155 gag tac ttg cag ctg gtc ttt ggc atc gag gtg gtg gaa gtg gtc cgc      3472
Glu Tyr Leu Gln Leu Val Phe Gly Ile Glu Val Val Glu Val Val Arg
                160                 165                 170 atc ggc cac ttg tac atc ctt gtc acc tgc ctg ggc ctc tcc tac gct      3520
Ile Gly His Leu Tyr Ile Leu Val Thr Cys Leu Gly Leu Ser Tyr Ala
            175                 180                 185 ggc ctg ctg ggc gac aat cag atc gtg ccc aag aca ggc ctc ctg ata      3568
Gly Leu Leu Gly Asp Asn Gln Ile Val Pro Lys Thr Gly Leu Leu Ile
        190                 195                 200 atc gtc ctg gcc ata atc gca aaa gag ggc gac tgt gcc cct gag gag      3616
Ile Val Leu Ala Ile Ile Ala Lys Glu Gly Asp Cys Ala Pro Glu Glu
    205                 210                 215 aaa atc tgg gag gag ctg agt gtg ttg gag gca tct gat ggg agg gag      3664
Lys Ile Trp Glu Glu Leu Ser Val Leu Glu Ala Ser Asp Gly Arg Glu
220                 225                 230                 235 gac agt gtc ttt gcg cat ccc agg aag ctg ctc acc caa gat ttg gtg      3712
Asp Ser Val Phe Ala His Pro Arg Lys Leu Leu Thr Gln Asp Leu Val
                240                 245                 250 cag gaa aac tac ctg gag tac cgg cag gtc ccc ggc agt gat cct gca      3760
Gln Glu Asn Tyr Leu Glu Tyr Arg Gln Val Pro Gly Ser Asp Pro Ala
            255                 260                 265 tgc tac gag ttc ctg tgg ggt cca agg gcc ctc gtt gaa acc agc tat      3808
Cys Tyr Glu Phe Leu Trp Gly Pro Arg Ala Leu Val Glu Thr Ser Tyr
        270                 275                 280
```

-continued

```
gtg aaa gtc ctg cac cat ttg cta aag atc agt gga ggg cct cac att    3856
Val Lys Val Leu His His Leu Leu Lys Ile Ser Gly Gly Pro His Ile
    285                 290                 295 ccc tac cca ccc ctg cat gaa tgg gct ttt aga gag ggg gaa gag tga    3904
Pro Tyr Pro Pro Leu His Glu Trp Ala Phe Arg Glu Gly Glu Glu
300                 305                 310 gtctgagcac gagttgcagc cagggccagt gggagggagt ctgggccagt gcaccttcca    3964
aggccctatc cattagtttc cactgcctcg tgtgacatga ggcccattct tcactctttg    4024
aagagagcag tcagtattgt tagtagtgag tttctgttct attggatgac tttgagattt    4084
atctttgttt cctgttggaa ttgttcaaat gttcctttta acggatggtt gaatgaactt    4144
cagcatccaa gtttatgaat gacagtagtc acacatagtg ctgtttatat agtttaggag    4204
taagagtgtt gttttttatt cagatttggg aaatccattc cattttgtga attgtgacaa    4264
ataacagcag tggaaaaagt atgtgcttag aattgtgaaa gaattagcag taaaatacat    4324
gagataaaga cctcaagaag ttaaaagata cttaattctt gccttatacc tcacttcatt    4384
ctgtaaattt gaaaaaaag cgtggatacc tggatatcct tggcttcttt gagaatttaa    4444
gagaaattaa atctgaataa ataattcttc ctgttcactg gctcatttat tttccattca    4504
ctcagcatct gctctgtgg                                                 4523
```

<210> SEQ ID NO 2
<211> LENGTH: 314
<212> TYPE: PRT
<213> ORGANISM: Homo sapiens

<400> SEQUENCE: 2

```
Met Pro Leu Glu Gln Arg Ser Gln His Cys Lys Pro Glu Glu Gly Leu
 1               5                  10                  15

Glu Ala Gln Gly Glu Ala Leu Gly Leu Val Gly Ala Gln Ala Pro Ala
            20                  25                  30

Thr Glu Gln Glu Thr Ala Ser Ser Ser Thr Leu Val Glu Val
        35                  40                  45

Thr Leu Arg Glu Val Pro Ala Ala Glu Ser Pro Ser Pro Pro His Ser
    50                  55                  60

Pro Gln Gly Ala Ser Thr Leu Pro Thr Thr Ile Asn Tyr Thr Leu Trp
65                  70                  75                  80

Ser Gln Ser Asp Glu Gly Ser Ser Asn Glu Glu Gln Glu Gly Pro Ser
                85                  90                  95

Thr Phe Pro Asp Leu Glu Thr Ser Phe Gln Val Ala Leu Ser Arg Lys
            100                 105                 110

Met Ala Glu Leu Val His Phe Leu Leu Leu Lys Tyr Arg Ala Arg Glu
        115                 120                 125

Pro Phe Thr Lys Ala Glu Met Leu Gly Ser Val Ile Arg Asn Phe Gln
    130                 135                 140

Asp Phe Phe Pro Val Ile Phe Ser Lys Ala Ser Glu Tyr Leu Gln Leu
145                 150                 155                 160

Val Phe Gly Ile Glu Val Val Glu Val Val Arg Ile Gly His Leu Tyr
                165                 170                 175

Ile Leu Val Thr Cys Leu Gly Leu Ser Tyr Ala Gly Leu Leu Gly Asp
            180                 185                 190

Asn Gln Ile Val Pro Lys Thr Gly Leu Leu Ile Ile Val Leu Ala Ile
        195                 200                 205

Ile Ala Lys Glu Gly Asp Cys Ala Pro Glu Glu Lys Ile Trp Glu Glu
    210                 215                 220
```

```
Leu Ser Val Leu Glu Ala Ser Asp Gly Arg Glu Asp Ser Val Phe Ala
225                 230                 235                 240

His Pro Arg Lys Leu Leu Thr Gln Asp Leu Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
        275                 280                 285

His Leu Leu Lys Ile Ser Gly Gly Pro His Ile Pro Tyr Pro Pro Leu
    290                 295                 300

His Glu Trp Ala Phe Arg Glu Gly Glu Glu
305                 310

<210> SEQ ID NO 3
<211> LENGTH: 9
<212> TYPE: PRT
<213> ORGANISM: Homo sapiens

<400> SEQUENCE: 3

Glu Val Val Arg Ile Gly His Leu Tyr
1               5

<210> SEQ ID NO 4
<211> LENGTH: 9
<212> TYPE: PRT
<213> ORGANISM: Homo sapiens

<400> SEQUENCE: 4

Val Arg Ile Gly His Leu Tyr Ile Leu
1               5

<210> SEQ ID NO 5
<211> LENGTH: 10
<212> TYPE: PRT
<213> ORGANISM: Homo sapiens

<400> SEQUENCE: 5

Val Val Arg Ile Gly His Leu Tyr Ile Leu
1               5                   10

<210> SEQ ID NO 6
<211> LENGTH: 8
<212> TYPE: PRT
<213> ORGANISM: Homo sapiens

<400> SEQUENCE: 6

Arg Ile Gly His Leu Tyr Ile Leu
1               5

<210> SEQ ID NO 7
<211> LENGTH: 24
<212> TYPE: DNA
<213> ORGANISM: Homo sapiens

<400> SEQUENCE: 7
gggtccaaat tgttggcttt cact                                   24

<210> SEQ ID NO 8
<211> LENGTH: 22
<212> TYPE: DNA
<213> ORGANISM: Homo sapiens
```

-continued

```
<400> SEQUENCE: 8
gaagaatgcc tcatgatccc ca                                              22

<210> SEQ ID NO 9
<211> LENGTH: 9
<212> TYPE: PRT
<213> ORGANISM: Homo sapiens

<400> SEQUENCE: 9

Glu Ala Asp Pro Thr Gly His Ser Tyr
1               5

<210> SEQ ID NO 10
<211> LENGTH: 9
<212> TYPE: PRT
<213> ORGANISM: Homo sapiens

<400> SEQUENCE: 10

Ser Ala Tyr Gly Glu Pro Arg Lys Leu
1               5

<210> SEQ ID NO 11
<211> LENGTH: 9
<212> TYPE: PRT
<213> ORGANISM: Homo sapiens

<400> SEQUENCE: 11

Glu Val Asp Pro Ile Gly His Leu Tyr
1               5

<210> SEQ ID NO 12
<211> LENGTH: 9
<212> TYPE: PRT
<213> ORGANISM: Homo sapiens

<400> SEQUENCE: 12

Phe Leu Trp Gly Pro Arg Ala Leu Val
1               5

<210> SEQ ID NO 13
<211> LENGTH: 10
<212> TYPE: PRT
<213> ORGANISM: Homo sapiens

<400> SEQUENCE: 13

Met Glu Val Asp Pro Ile Gly His Leu Tyr
1               5                   10

<210> SEQ ID NO 14
<211> LENGTH: 9
<212> TYPE: PRT
<213> ORGANISM: Homo sapiens

<400> SEQUENCE: 14

Ala Ala Arg Ala Val Phe Leu Ala Leu
1               5

<210> SEQ ID NO 15
<211> LENGTH: 8
<212> TYPE: PRT
<213> ORGANISM: Homo sapiens

<400> SEQUENCE: 15

Tyr Arg Pro Arg Pro Arg Arg Tyr
```

```
 1               5

<210> SEQ ID NO 16
<211> LENGTH: 10
<212> TYPE: PRT
<213> ORGANISM: Homo sapiens

<400> SEQUENCE: 16

Ser Pro Ser Ser Asn Arg Ile Arg Asn Thr
 1               5                  10

<210> SEQ ID NO 17
<211> LENGTH: 9
<212> TYPE: PRT
<213> ORGANISM: Homo sapiens

<400> SEQUENCE: 17

Val Leu Pro Asp Val Phe Ile Arg Cys
 1               5

<210> SEQ ID NO 18
<211> LENGTH: 10
<212> TYPE: PRT
<213> ORGANISM: Homo sapiens

<400> SEQUENCE: 18

Val Leu Pro Asp Val Phe Ile Arg Cys Val
 1               5                  10

<210> SEQ ID NO 19
<211> LENGTH: 9
<212> TYPE: PRT
<213> ORGANISM: Homo sapiens

<400> SEQUENCE: 19

Glu Glu Lys Leu Ile Val Val Leu Phe
 1               5

<210> SEQ ID NO 20
<211> LENGTH: 9
<212> TYPE: PRT
<213> ORGANISM: Homo sapiens

<400> SEQUENCE: 20

Glu Glu Lys Leu Ser Val Val Leu Phe
 1               5

<210> SEQ ID NO 21
<211> LENGTH: 10
<212> TYPE: PRT
<213> ORGANISM: Homo sapiens

<400> SEQUENCE: 21

Ala Cys Asp Pro His Ser Gly His Phe Val
 1               5                  10

<210> SEQ ID NO 22
<211> LENGTH: 10
<212> TYPE: PRT
<213> ORGANISM: Homo sapiens

<400> SEQUENCE: 22

Ala Arg Asp Pro His Ser Gly His Phe Val
 1               5                  10
```

```
<210> SEQ ID NO 23
<211> LENGTH: 9
<212> TYPE: PRT
<213> ORGANISM: Homo sapiens

<400> SEQUENCE: 23

Ser Tyr Leu Asp Ser Gly Ile His Phe
 1               5

<210> SEQ ID NO 24
<211> LENGTH: 9
<212> TYPE: PRT
<213> ORGANISM: Homo sapiens

<400> SEQUENCE: 24

Ser Tyr Leu Asp Ser Gly Ile His Ser
 1               5

<210> SEQ ID NO 25
<211> LENGTH: 9
<212> TYPE: PRT
<213> ORGANISM: Homo sapiens

<400> SEQUENCE: 25

Met Leu Leu Ala Val Leu Tyr Cys Leu
 1               5

<210> SEQ ID NO 26
<211> LENGTH: 9
<212> TYPE: PRT
<213> ORGANISM: Homo sapiens

<400> SEQUENCE: 26

Tyr Met Asn Gly Thr Met Ser Gln Val
 1               5

<210> SEQ ID NO 27
<211> LENGTH: 9
<212> TYPE: PRT
<213> ORGANISM: Homo sapiens

<400> SEQUENCE: 27

Ala Phe Leu Pro Trp His Arg Leu Phe
 1               5

<210> SEQ ID NO 28
<211> LENGTH: 9
<212> TYPE: PRT
<213> ORGANISM: Homo sapiens

<400> SEQUENCE: 28

Ser Glu Ile Trp Arg Asp Ile Asp Phe
 1               5

<210> SEQ ID NO 29
<211> LENGTH: 9
<212> TYPE: PRT
<213> ORGANISM: Homo sapiens

<400> SEQUENCE: 29

Tyr Glu Ile Trp Arg Asp Ile Asp Phe
 1               5

<210> SEQ ID NO 30
```

<211> LENGTH: 15
<212> TYPE: PRT
<213> ORGANISM: Homo sapiens

<400> SEQUENCE: 30

Gln Asn Ile Leu Leu Ser Asn Ala Pro Leu Gly Pro Gln Phe Pro
 1               5                  10                  15

<210> SEQ ID NO 31
<211> LENGTH: 15
<212> TYPE: PRT
<213> ORGANISM: Homo sapiens

<400> SEQUENCE: 31

Asp Tyr Ser Tyr Leu Gln Asp Ser Asp Pro Asp Ser Phe Gln Asp
 1               5                  10                  15

<210> SEQ ID NO 32
<211> LENGTH: 10
<212> TYPE: PRT
<213> ORGANISM: Homo sapiens

<400> SEQUENCE: 32

Glu Ala Ala Gly Ile Gly Ile Leu Thr Val
 1               5                  10

<210> SEQ ID NO 33
<211> LENGTH: 9
<212> TYPE: PRT
<213> ORGANISM: Homo sapiens

<400> SEQUENCE: 33

Ala Ala Gly Ile Gly Ile Leu Thr Val
 1               5

<210> SEQ ID NO 34
<211> LENGTH: 9
<212> TYPE: PRT
<213> ORGANISM: Homo sapiens

<400> SEQUENCE: 34

Ile Leu Thr Val Ile Leu Gly Val Leu
 1               5

<210> SEQ ID NO 35
<211> LENGTH: 9
<212> TYPE: PRT
<213> ORGANISM: Homo sapiens

<400> SEQUENCE: 35

Lys Thr Trp Gly Gln Tyr Trp Gln Val
 1               5

<210> SEQ ID NO 36
<211> LENGTH: 9
<212> TYPE: PRT
<213> ORGANISM: Homo sapiens

<400> SEQUENCE: 36

Ile Thr Asp Gln Val Pro Phe Ser Val
 1               5

<210> SEQ ID NO 37
<211> LENGTH: 9
<212> TYPE: PRT

<213> ORGANISM: Homo sapiens

<400> SEQUENCE: 37

Tyr Leu Glu Pro Gly Pro Val Thr Ala
 1               5

<210> SEQ ID NO 38
<211> LENGTH: 10
<212> TYPE: PRT
<213> ORGANISM: Homo sapiens

<400> SEQUENCE: 38

Leu Leu Asp Gly Thr Ala Thr Leu Arg Leu
 1               5                  10

<210> SEQ ID NO 39
<211> LENGTH: 10
<212> TYPE: PRT
<213> ORGANISM: Homo sapiens

<400> SEQUENCE: 39

Val Leu Tyr Arg Tyr Gly Ser Phe Ser Val
 1               5                  10

<210> SEQ ID NO 40
<211> LENGTH: 9
<212> TYPE: PRT
<213> ORGANISM: Homo sapiens

<400> SEQUENCE: 40

Leu Tyr Val Asp Ser Leu Phe Phe Leu
 1               5

<210> SEQ ID NO 41
<211> LENGTH: 12
<212> TYPE: PRT
<213> ORGANISM: Homo sapiens

<400> SEQUENCE: 41

Lys Ile Ser Gly Gly Pro Arg Ile Ser Tyr Pro Leu
 1               5                  10

<210> SEQ ID NO 42
<211> LENGTH: 9
<212> TYPE: PRT
<213> ORGANISM: Homo sapiens

<400> SEQUENCE: 42

Tyr Met Asp Gly Thr Met Ser Gln Val
 1               5

<210> SEQ ID NO 43
<211> LENGTH: 11
<212> TYPE: PRT
<213> ORGANISM: Homo sapiens

<400> SEQUENCE: 43

Ser Leu Leu Met Trp Ile Thr Gln Cys Phe Leu
 1               5                  10

<210> SEQ ID NO 44
<211> LENGTH: 9
<212> TYPE: PRT
<213> ORGANISM: Homo sapiens

```
<400> SEQUENCE: 44

Ser Leu Leu Met Trp Ile Thr Gln Cys
  1               5

<210> SEQ ID NO 45
<211> LENGTH: 9
<212> TYPE: PRT
<213> ORGANISM: Homo sapiens

<400> SEQUENCE: 45

Gln Leu Ser Leu Leu Met Trp Ile Thr
  1               5

<210> SEQ ID NO 46
<211> LENGTH: 20
<212> TYPE: DNA
<213> ORGANISM: Homo sapiens

<400> SEQUENCE: 46
cctacctgct gccctgacca                                            20

<210> SEQ ID NO 47
<211> LENGTH: 20
<212> TYPE: DNA
<213> ORGANISM: Homo sapiens

<400> SEQUENCE: 47
cctaaggact gtggggagga                                            20

<210> SEQ ID NO 48
<211> LENGTH: 20
<212> TYPE: DNA
<213> ORGANISM: Homo sapiens

<400> SEQUENCE: 48
ccaactaagc catcttccta                                            20

<210> SEQ ID NO 49
<211> LENGTH: 20
<212> TYPE: DNA
<213> ORGANISM: Homo sapiens

<400> SEQUENCE: 49
gtgacaagga tctacaagtg                                            20

<210> SEQ ID NO 50
<211> LENGTH: 20
<212> TYPE: DNA
<213> ORGANISM: Homo sapiens

<400> SEQUENCE: 50
ccagtcaggt gacaaggatg                                            20

<210> SEQ ID NO 51
<211> LENGTH: 20
<212> TYPE: DNA
<213> ORGANISM: Homo sapiens

<400> SEQUENCE: 51
cctgtctagg gcacgatctg                                            20

<210> SEQ ID NO 52
<211> LENGTH: 20
```

```
<212> TYPE: DNA
<213> ORGANISM: Homo sapiens

<400> SEQUENCE: 52
ctcctaaggg gcacagtcgc                                                    20

<210> SEQ ID NO 53
<211> LENGTH: 20
<212> TYPE: DNA
<213> ORGANISM: Homo sapiens

<400> SEQUENCE: 53
tcagatgcct acaacacact                                                    20

<210> SEQ ID NO 54
<211> LENGTH: 20
<212> TYPE: DNA
<213> ORGANISM: Homo sapiens

<400> SEQUENCE: 54
ggaccctaca ggaactcgta                                                    20

<210> SEQ ID NO 55
<211> LENGTH: 20
<212> TYPE: DNA
<213> ORGANISM: Homo sapiens

<400> SEQUENCE: 55
cgttggaggt cagagaacag                                                    20

<210> SEQ ID NO 56
<211> LENGTH: 22
<212> TYPE: DNA
<213> ORGANISM: Homo sapiens

<400> SEQUENCE: 56
gccctccact gatctttagc aa                                                 22
```

MAGE-A12 ANTIGENIC PEPTIDES AND USES THEREOF

RELATED APPLICATIONS

This application claims priority under 35 U.S.C. §119 to U.S. provisional application Ser. No. 60/160,374, filed Oct. 19, 1999, and to U.S. provisional application Ser. No. 60/179,570, filed Feb. 1, 2000.

FIELD OF THE INVENTION

This invention relates to polypeptides and encoded nucleic acid molecules which are expressed preferentially in tumors, including melanomas, bladder carcinomas, renal carcinomas, lung carcinomas, esophageal carcinomas, etc. The nucleic acid molecules and encoded polypeptides are useful in, inter alia, diagnostic and therapeutic contexts.

BACKGROUND OF THE INVENTION

The phenotypic changes which distinguish a tumor cell from its normal counterpart are often the result of one or more changes to the genome of the cell. The genes which are expressed in tumor cells, but not in normal counterparts, can be termed "tumor associated" genes. These tumor associated genes are markers for the tumor phenotype. The expression of tumor associated genes can also be an essential event in the process of tumorigenesis.

Typically, the host recognizes as foreign the tumor associated genes which are not expressed in normal non-tumorigenic cells. Thus, the expression of tumor associated genes can provoke an immune response against the tumor cells by the host. Tumor associated genes can also be expressed in normal cells within certain tissues without provoking an immune response. In such tissues, expression of the gene and/or presentation of an ordinarily immunologically recognizable fragment of the protein product on the cell surface may not provoke an immune response because the immune system does not "see" the cells inside these immunologically privileged tissues. Examples of immunologically privileged tissues include brain and testis.

The discovery of tumor associated expression of a gene provides a means of identifying a cell as a tumor cell. Diagnostic compounds can be based on the tumor associated gene, and used to determine the presence and location of tumor cells. Further, when the tumor associated gene contributes to an aspect of the tumor phenotype (e.g., unregulated growth or metastasis), the tumor associated gene can be used to provide therapeutics such as antisense nucleic acids which can reduce or substantially eliminate expression of that gene, thereby reducing or substantially eliminating the phenotypic aspect which depends on the expression of the particular tumor associated gene.

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., Advanced Immunoloy (J. P. Lipincott Company, 1987), especially chapters 6–10. The interaction of T cells and complexes of HLA/peptide is restricted, requiring a T cell specific for a particular combination of an HLA molecule and a peptide. If a specific T cell is not present, there is no T cell response even if its partner complex is present. Similarly, there is no response if the specific complex is absent, but the T cell is present. The mechanism is involved in the immune system's response to foreign materials, in autoimmune pathologies, and in responses to cellular abnormalities. Much work has focused on the mechanisms by which proteins are processed into the HLA binding peptides. See, in this regard, Barinaga, Science 257: 880, 1992; Fremont et al., Science 257: 919, 1992; Matsumura et al., Science 257: 927, 1992; Latron et al., Science 257: 964, 1992.

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., J. Exp. Med. 176:1453–1457, 1992; van der Bruggen et al., Science 254: 1643,1991; De Plaen et al., Immunogenetics 40:360–369, 1994 and U.S. Pat. No. 5,342,774 for further information on this family of genes.

In U.S. Pat. No. 5,405,940, the disclosure of which is incorporated by reference, nonapeptides are taught which are presented by the HLA-A1 molecule. The reference teaches that given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. Pat. No. 5,629,166, incorporated by reference, the fact that the MAGE-1 expression product is processed to a second TRA is disclosed. This second TRA is presented by HLA-Cw16 molecules, also known as HLA-C*1601. The disclosure shows that a given TRAP can yield a plurality of TRAs.

In U.S. Pat. No. 5,487,974, incorporated by reference herein, tyrosinase is described as a tumor rejection antigen precursor. This reference discloses that a molecule which is produced by some normal cells (e.g., melanocytes), is processed in tumor cells to yield a tumor rejection antigen that is presented by HLA-A2 molecules.

In U.S. Pat. No. 5,620,886, incorporated herein by reference in its entirety, a second TRA, not derived from tyrosinase is taught to be presented by HLA-A2 molecules. The TRA is derived from a TRAP, but is coded for by a known MAGE gene. This disclosure shows that a particular HLA molecule may present TRAs derived from different sources.

Additional TRAPs are disclosed in U.S. Pat. Nos. 5,571,711, 5,610,013, 5,587,289 and 5,589,334, as well as PCT publication WO96/10577. The TRAPs are processed to tumor rejection antigens, which are presented by a variety of HLA molecules.

There exist many patients who would benefit from therapy which includes additional antigenic peptides, either because the patient's tumor does not express previously known antigenic peptides, or because the patient does not express the appropriate HLA molecule. Accordingly, there is a need for the identification of additional tumor associated antigens which contain epitopes presented by MHC class I molecules and recognized by CD8+ lymphocytes.

SUMMARY OF THE INVENTION

It now has been discovered that the human MAGE-A12 gene (SEQ ID NO: 1) encodes a tumor rejection antigen presented by HLA-Cw*07. Peptides derived from the MAGE-A12 polypeptide (SEQ ID NO:2), when presented by an antigen presenting cell having an HLA class I molecule, effectively induce the activation and proliferation of CD8+ cytotoxic T lymphocytes.

According to one aspect of the invention, an isolated MAGE-A12 HLA class 1-binding peptide is provided. The peptide includes the amino acid sequence of SEQ ID NO:6, or a functional variant thereof which binds HLA class I molecules. The functional variant includes one or more amino acid additions, substitutions or deletions. In certain embodiments, the isolated MAGE-A12 HLA class 1-binding peptide includes an amino acid sequence selected from the group consisting of SEQ ID NO:4, SEQ ID NO:5, fragments thereof, and functional variants thereof. In preferred embodiments, the isolated peptide consists of an amino acid sequence selected from the group consisting of SEQ ID NO:4, SEQ ID NO:5, SEQ ID NO:6, fragments thereof, and functional variants thereof. The isolated MAGE-A12 HLA class I-binding peptide preferably is not the full length MAGE-A12 polypeptide sequence.

According to another aspect of the invention, an isolated MAGE-A12 HLA class I binding peptide is provided which includes a fragment of the amino acid sequence of SEQ ID NO:2 which binds HLA Cw*07, or a functional variant thereof. The functional variant includes one or more amino acid additions, substitutions or deletions. The functional variant binds HLA Cw*07. Preferred embodiments include SEQ ID NO:3, SEQ ID NO:4, SEQ ID NO:5, and SEQ ID NO:6.

In some embodiments, the foregoing isolated MAGE-A12 HLA class 1-binding peptides are non-hydrolyzable. Preferably the non-hydrolyzable peptide is selected from the group consisting of peptides comprising D-amino acids, peptides comprising a
-psi [CH₂NH]-reduced amide peptide bond, peptides comprising a
-psi[COCH₂]-ketomethylene peptide bond, peptides comprising a
-psi[CH(CN)NH]-(cyanomethylene)amino peptide bond, peptides comprising a
-psi[CH₂CH(OH)]-hydroxyethylene peptide bond, peptides comprising a -psi[CH₂O]-peptide bond, and peptides comprising a -psi[CH₂S]-thiomethylene peptide bond.

Also provided according to an aspect of the invention are compositions including the foregoing isolated MAGE-A12 HLA class I-binding peptides and one or more isolated HLA class I- or class II-binding peptides of non-MAGE-A12 tumor antigens. Preferably the MAGE-A12 HLA class I-binding peptides and the non-MAGE-A12 HLA binding peptides are combined as a polytope polypeptide.

According to another aspect of the invention, isolated nucleic acids encoding the foregoing peptides are provided. The nucleic acids do not encode full length MAGE-A12. In certain embodiments, the nucleic acids comprise a fragment of the nucleotide sequence of SEQ ID NO: 1. Expression vectors are also provided according to the invention. The expression vectors include the isolated foregoing nucleic acids operably linked to a promoter. In certain embodiments, the expression vectors also include a nucleic acid which encodes an HLA-Cw*07 molecule. In another aspect of the invention, host cells transfected or transformed with the foregoing nucleic acids or expression vectors are provided. In certain embodiments, the host cells also express an HLA-Cw*07 molecule.

According to yet another aspect of the invention, methods for enriching selectively a population of T lymphocytes with T lymphocytes specific for a MAGE-A12 HLA binding peptide are provided. The methods include contacting a source of T lymphocytes which contains a population of T lymphocytes with an agent presenting a complex of the MAGE-A12 HLA binding peptide and an HLA molecule in an amount sufficient to selectively enrich the population of T lymphocytes with the T lymphocytes specific for a MAGE-A12 HLA binding peptide. In certain embodiments, the agent is an antigen presenting cell contacted with a MAGE-A12 protein or an HLA binding fragment thereof. In other embodiments, the MAGE-A12 HLA binding peptide is selected from the group consisting of (i) peptides which consist of a fragment of the amino acid sequence of SEQ ID NO:2, (ii) peptides which comprise the amino acid sequence of SEQ ID NO:6, and (iii) functional variants of the peptides of (i) and (ii).

According to still another aspect of the invention, methods for diagnosing a disorder characterized by expression of MAGE-A 12 are provided. The methods include contacting a biological sample isolated from a subject with an agent that is specific for a MAGE-A12 HLA binding peptide, and determining the interaction between the agent and the MAGE-A12 HLA binding peptide as a determination of the disorder. Preferably the MAGE-A 12 HLA binding peptide is selected from the group consisting of (i) peptides which consist of a fragment of the amino acid sequence of SEQ ID NO:2, (ii) peptides which comprise the amino acid sequence of SEQ ID NO:6, and (iii) functional variants of the peptides of (i) and (ii).

In another aspect of the invention, methods for diagnosing a disorder characterized by expression of a MAGE-A12 HLA binding peptide are provided. The methods include contacting a biological sample isolated from a subject with an agent that binds the complex and determining binding between the complex and the agent as a determination of the disorder. In certain embodiments, the MAGE-A12 HLA binding peptide is selected from the group consisting (i) peptides which consist of a fragment of the amino acid sequence of SEQ ID NO:2, (ii) peptides which comprise the amino acid sequence of SEQ ID NO:6, and (iii) functional variants of the peptides of (i) and (ii).

According to still another aspect of the invention, methods for treating a subject having a disorder characterized by expression of MAGE-A 12 are provided. The methods include administering to the subject an amount of a MAGE-A12 HLA binding peptide sufficient to ameliorate the disorder. In certain embodiments, the MAGE-A12 HLA binding peptide is selected from the group consisting of (i) peptides which consist of a fragment of the amino acid sequence of SEQ ID NO:2, (ii) peptides which comprise the amino acid sequence of SEQ ID NO:6, and (iii) functional variants of the peptides of (i) and (ii).

According to another aspect of the invention, methods for treating a subject having a disorder characterized by expression of MAGE-A12 are provided. The methods include administering to the subject an amount of a composition which included an isolated MAGE-A12 HLA class I-binding peptide and an isolated HLA class I- or class U-binding peptide of a non-MAGE-A12 tumor antigen sufficient to ameliorate the disorder.

According to yet another aspect of the invention, methods for treating a subject having a disorder characterized by expression of MAGE-A2 are provided. The methods include administering to the subject an amount of an agent which enriches selectively in the subject the presence of complexes of an HLA molecule and a MAGE-A12 HLA binding peptide, sufficient to ameliorate the disorder. In certain embodiments, the agent includes a MAGE-A12 HLA binding peptide. In preferred embodiments, the MAGE-A12 HLA binding peptide is selected from the group consisting of (i) peptides which consist of a fragment of the amino acid sequence of SEQ ID NO:2, (ii) peptides which comprise the amino acid sequence of SEQ ID NO:6, and (iii) functional variants of the peptides of (i) and (ii).

According to a further aspect of the invention, methods for treating a subject having a disorder characterized by expression of MAGE-A12 are provided. The methods include administering to the subject an amount of autologous T lymphocytes sufficient to ameliorate the disorder, wherein the T lymphocytes are specific for complexes of an HLA molecule and a MAGE-A12 HLA binding peptide. In some embodiments, the MAGE-A12 HLA binding peptide is selected from the group consisting of (i) peptides which consist of a fragment of the amino acid sequence of SEQ ID NO:2, (ii) peptides which comprise the amino acid sequence of SEQ ID NO:6, and (iii) functional variants of the peptides of (i) and (ii).

Also provided according to another aspect of the invention are methods for identifying functional variants of a MAGE-A12 HLA binding peptide. The methods include selecting a MAGE-A12 HLA binding peptide, an HLA binding molecule which binds the MAGE-A12 HLA class I binding peptide, and a T cell which is stimulated by the MAGE-A12 HLA binding peptide presented by the HLA binding molecule; mutating a first amino acid residue of the MAGE-A12 HLA binding peptide to prepare a variant peptide; and determining the binding of the variant peptide to HLA binding molecule and the stimulation of the T cell, wherein binding of the variant peptide to the HLA binding molecule and stimulation of the T cell by the variant peptide presented by the HLA binding molecule indicates that the variant peptide is a functional variant. In certain embodiments, the MAGE-A12 HLA binding peptide is selected from the group consisting of (i) peptides which consist of a fragment of the amino acid sequence of SEQ ID NO:2, and (ii) peptides which comprise the amino acid sequence of SEQ ID NO:6. In other embodiments, the methods include the step of comparing the stimulation of the T cell by the MAGE-A12 HLA binding peptide and the stimulation of the T cell by the functional variant as a determination of the effectiveness of the stimulation of the T cell by the functional variant. Also provided are isolated functional variants of a MAGE-A12 HLA binding peptide identified by the methods.

According to another aspect of the invention, isolated polypeptides are provided which bind selectively the foregoing MAGE-A12 HLA binding peptides, provided that the isolated polypeptides are not HLA molecules. In some embodiments, the isolated polypeptides are antibodies, preferably monoclonal antibodies. In other embodiments the isolated polypeptides are antibody fragments selected from the group consisting of Fab fragments, F(ab)$_2$ fragments or fragments including a CDR3 region selective for a MAGE-A12 HLA binding peptide.

According to still another aspect of the invention, isolated T lymphocytes which selectively bind a complex of an HLA molecule and a MAGE-A 12 HLA binding peptide are provided. In some embodiments, the MAGE-A12 HLA binding peptide is selected from the group consisting of (i) peptides which consist of a fragment of the amino acid sequence of SEQ ID NO:2, (ii) peptides which comprise the amino acid sequence of SEQ ID NO:6, and (iii) functional variants of the peptides of (i) and (ii).

According to a further aspect of the invention, isolated antigen presenting cells which include a complex of an HLA molecule and a MAGE-A 12 HLA binding peptide are provided. In certain embodiments, the MAGE-A12 HLA binding peptide is selected from the group consisting of (i) peptides which consist of a fragment of the amino acid sequence of SEQ ID NO:2, (ii) peptides which comprise the amino acid sequence of SEQ ID NO:6, and (iii) functional variants of the peptides of (i) and (ii).

According to yet another aspect of the invention, methods for identifying a candidate mimetic of a MAGE-A12 HLA binding peptide are provided. The methods include providing a HLA molecule which binds the MAGE-A12 HLA binding peptide, contacting the HLA molecule with a test molecule, and determining the binding of the test molecule to the HLA molecule, wherein a test molecule which binds to the HLA molecule is a candidate mimetic of the MAGE-A12 HLA binding peptide. In some embodiments, the methods include forming a complex of the HLA molecule and the candidate mimetic, contacting the complex with a T cell which binds to a complex of an HLA molecule and the MAGE-A 12 HLA binding peptide, and assaying activation of the T cell. In certain of these methods, activation of the T cell is indicated by a property selected from the group consisting of proliferation of the T cell, interferon-γ production by the T cell, tumor necrosis factor production by the T cell, and cytolysis of a target cell by the T cell.

According to a further aspect of the invention vaccine compositions are provided. The vaccine compositions can include the foregoing MAGE-A12 HLA binding peptides, the foregoing T lymphocytes, the foregoing antigen presenting cells, and/or the foregoing isolated nucleic acid molecules. In certain embodiments, the foregoing vaccine compositions include an adjuvant and/or a pharmaceutically acceptable carrier.

In another aspect of the invention, protein microatrays that include one or more isolated MAGE-A12 HLA class 1-binding peptides, or functional variants thereof that bind HLA class I molecules, are provided. The functional variants include one or more amino acid additions, substitutions or deletions. In some embodiments the isolated MAGE-A12 HLA class I-binding peptides include the amino acid sequence of SEQ ID NO:6. In other embodiments the isolated MAGE-A12 HLA class I-binding peptides include an amino acid sequence selected from the group consisting of SEQ ID NO:4, SEQ ID NO:5, and functional variants thereof. The use of such microarrays in diagnostic applications, particularly for diagnosing cancer, also is provided. The diagnostic methods include contacting the protein microarray with a biological sample isolated from a subject suspected of having the disorder, and determining the binding of a constituent of the biological sample to the isolated MAGE-A12 HLA class I binding peptide. In certain embodiments the constituent of the biological sample is selected from the group consisting of an antibody, a T lymphocyte, and a HLA molecule. Preferably the disorder is cancer.

The invention also provides pharmaceutical preparations containing any one or more of the compositions described herein. Such pharmaceutical preparations can include pharmaceutically acceptable diluent carriers or excipients. The use of such compositions in the preparation of medicaments, particularly medicaments for the treatment of cancer also is provided.

In the foregoing methods and compositions, the HLA molecule preferably is HLA Cw*07 and more preferably is HLA Cw*0701. Disorders as used herein include cancers, such as bladder carcinomas, melanomas, esophageal carcinomas, lung carcinomas, head and neck carcinomas, breast carcinomas, colorectal carcinomas, myelomas, brain tumors, sarcomas, prostate carcinomas and renal carcinomas.

These and other objects of the invention will be described in further detail in connection with the detailed description of the invention.

DETAILED DESCRIPTION OF THE INVENTION

Figure 1:
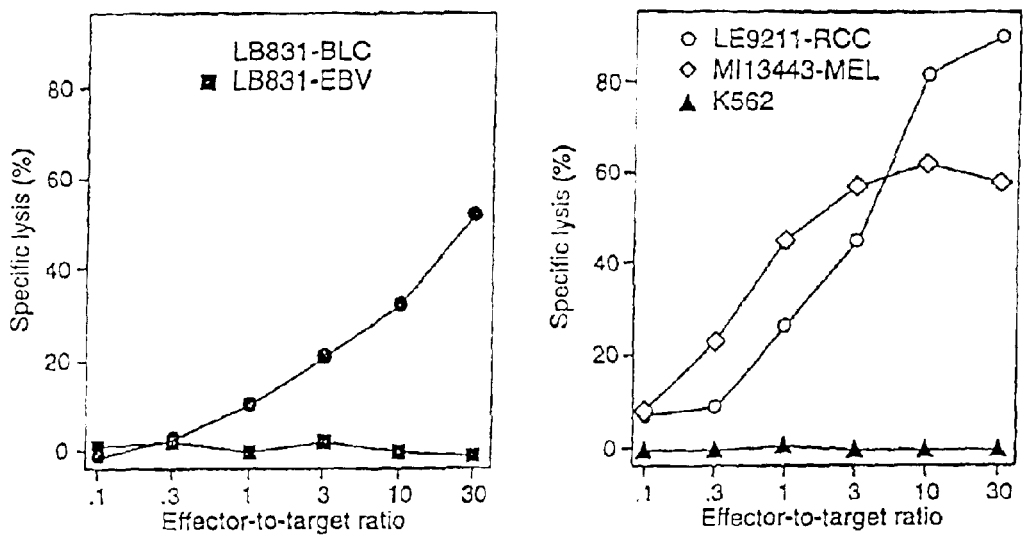
FIG. 1 depicts the recognition of autologous and allogeneic HLA-Cw*07-positive tumor cell lines by CTL 501D/19: (A) lysis, (B) TNF release.
Figure 1:
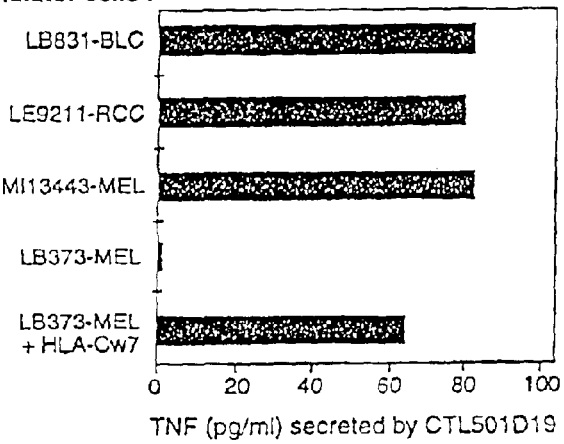

The invention provides isolated MAGE-A12 peptides, some of which are presented by HLA class I molecules, which peptides stimulate the proliferation and activation of CD8+ T lymphocytes. Such peptides are referred to herein as "MAGE-A12 immunogenic polypeptides" and "MAGE-A12 HLA class I binding peptides" and "MAGE-A12 HLA peptides", and the like. Hence, one aspect of the invention is an isolated peptide which includes the amino acid sequence of SEQ ID NO:6.

The examples below show the isolation of peptides which are MAGE-A12 HLA binding peptides. These exemplary peptides are processed translation products of the nucleic acid of SEQ ID NO: 1. As such, it will be appreciated by one of ordinary skill in the art that the translation products from which a MAGE-A12 immunogenic polypeptide is processed to a final form for presentation may be of any length or sequence so long as they encompass an HLA binding peptide. In certain instances, the HLA binding peptides include a MAGE-A12 HLA binding peptide having an amino acid sequence as set forth in SEQ ID NOs:4, 5 or 6. As demonstrated in the examples below, peptides or proteins as small as 8 amino acids are appropriately processed, presented by HLA class I molecules and effective in stimulating CD8+ T lymphocytes. The peptide of SEQ ID NOs:4, 5 or 6 may have one, two, three, four, five, six, seven, eight, nine, ten, or more amino acids added to either or both ends. The added amino acids can correspond to the MAGE-A 12 polypeptide (SEQ ID NO:2), or can be unrelated. As is well known in the art, the antigenic portion of such a peptide is cleaved out under physiological conditions for presentation by HLA class I molecules.

Additional HLA binding peptides derived from the MAGE-A12 polypeptide may provoke an immune response when presented by HLA Cw*07 molecules. The invention embraces all such immunogenic fragments of the MAGE-A 12 polypeptide.

As noted above, the invention embraces functional variants of the MAGE-A12 HLA binding peptides. As used herein, a "functional variant" or "variant" of a MAGE-A12 HLA binding peptide is a molecule which contains one or more modifications to the primary amino acid sequence of the MAGE-A 12 HLA binding peptide and retains the HLA class I binding properties disclosed herein, as well as the ability to stimulate proliferation and/or activation of CD8+ T lymphocytes. Modifications which create a MAGE-A12 immunogenic polypeptide functional variant can be made for example 1) to enhance a property of a MAGE-A12 HLA binding peptide, such as peptide stability in an expression system or the stability of protein—protein binding such as HLA-peptide binding; 2) to provide a novel activity or property to a MAGE-A12 immunogenic polypeptide, such as addition of an antigenic epitope or addition of a detectable moiety; or 3) to provide a different amino acid sequence that produces the same or similar T cell stimulatory properties. Modifications to a MAGE-A12 HLA binding peptide can be made to a nucleic acid which encodes the peptide, and can include deletions, point mutations, truncations, amino acid substitutions and additions of amino acids. Alternatively, modifications can be made directly to the polypeptide, such as by cleavage, addition of a linker molecule, addition of a detectable moiety, such as biotin, addition of a fatty acid, substitution of one amino acid for another and the like. Modifications also embrace fusion proteins comprising all or part of the MAGE-A12 immunogenic polypeptide amino acid sequence.

The amino acid sequence of MAGE-A12 immunogenic polypeptides may be of natural or non-natural origin, that is, they may comprise a natural MAGE-A12 immunogenic polypeptide molecule or may comprise a modified sequence as long as the amino acid sequence retains the ability to stimulate cytolytic T cells when presented and retains the property of binding to an HLA class I molecule such as an HLA Cw*07 molecule. For example, MAGE-A12 immunogenic polypeptides in this context may be fusion proteins of a MAGE-A12 HLA binding peptide and unrelated amino acid sequences, synthetic peptides of amino acid sequences shown in SEQ ID NOs:4, 5, and 6, labeled peptides, peptides isolated from patients with a MAGE-A12 expressing cancer, peptides isolated from cultured cells which express MAGE-A12, peptides coupled to nonpeptide molecules (for example in certain drug delivery systems) and other molecules which include the amino acid sequence of SEQ ID NO:6.

Preferably, MAGE-A12 HLA binding peptides are non-hydrolyzable. To provide such peptides, one may select MAGE-A 12 HLA binding peptides from a library of non-hydrolyzable peptides, such as peptides containing one or more D-amino acids or peptides containing one or more non-hydrolyzable peptide bonds linking amino acids. Alternatively, one can select peptides which are optimal for inducing CD8+ T lymphocytes and then modify such peptides as necessary to reduce the potential for hydrolysis by proteases. For example, to determine the susceptibility to proteolytic cleavage, peptides may be labeled and incubated with cell extracts or purified proteases and then isolated to determine which peptide bonds are susceptible to proteolysis, e.g., by sequencing peptides and proteolytic fragments. Alternatively, potentially susceptible peptide bonds can be identified by comparing the amino acid sequence of a MAGE-A 12 immunogenic polypeptide with the known cleavage site specificity of a panel of proteases. Based on the results of such assays, individual peptide bonds which are susceptible to proteolysis can be replaced with non-hydrolyzable peptide bonds by in vitro synthesis of the peptide.

Many non-hydrolyzable peptide bonds are known in the art, along with procedures for synthesis of peptides containing such bonds. Non-hydrolyzable bonds include -psi [CH$_2$NH]-reduced amide peptide bonds, -psi[COCH$_2$]-ketomethylene peptide bonds, -psi[CH(CN)NH]-(cyanomethylene)amino peptide bonds, -psi[CH$_2$CH(OH)]-hydroxyethylene peptide bonds, -psi[CH$_2$O]-peptide bonds, and -psi[CH$_2$S]-thiomethylene peptide bonds.

Nonpeptide analogs of peptides, e.g., those which provide a stabilized structure or lessened biodegradation, are also contemplated. Peptide mimetic analogs can be prepared based on a selected MAGE-A12 HLA binding peptide by replacement of one or more residues by nonpeptide moieties. Preferably, the nonpeptide moieties permit the peptide to retain its natural confirmation, or stabilize a preferred, e.g., bioactive, confirmation. One example of methods for preparation of nonpeptide mimetic analogs from peptides is described in Nachman et al., *Regul. Pept.* 57:359–370 (1995). Peptide mimetics also can be selected from libraries of synthetic compounds (e.g. combinatorial libraries of small organic molecules) or natural molecules according to the HLA binding properties and/or T cell stimulatory properties of such molecule. Assays for identification of mimetics of a MAGE-A12 immunogenic polypeptide from libraries such as binding assays are well known in the art. Peptide as used herein embraces all of the foregoing.

If a variant involves a change to an amino acid of a MAGE-A12 immunogenic polypeptide (e.g., SEQ ID NOs:4, 5 or 6), functional variants of the MAGE-A12 immunogenic polypeptide having conservative amino acid substitutions typically will be preferred, i.e., substitutions which retain a property of the original amino acid such as charge, hydrophobicity, conformation, etc. Examples of conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Other methods for identifying functional variants of the MAGE-A12 immunogenic polypeptides are provided in a published PCT application of Strominger and Wucherpfennig (US/96/03182). These methods rely upon the development of amino acid sequence motifs to which potential epitopes may be compared. Each motif describes a finite set of amino acid sequences in which the residues at each (relative) position may be (a) restricted to a single residue, (b) allowed to vary amongst a restricted set of residues, or (c) allowed to vary amongst all possible residues. For example, a motif might specify that the residue at a first position may be any one of the residues valine, leucine, isoleucine, methionine, or phenylalanine; that the residue at the second position must be histidine; that the residue at the third position may be any amino acid residue; that the residue at the fourth position may be any one of the residues valine, leucine, isoleucine, methionine, phenylalanine, tyrosine or tryptophan; and that the residue at the fifth position must be lysine.

Sequence motifs for MAGE-A12 HLA binding peptide functional variants can be developed by analysis of the binding domains or binding pockets of major histocompatibility complex HLA-Cw proteins and/or the T cell receptor ("TCR") contact points of the MAGE-A12 immunogenic polypeptides disclosed herein. By providing a detailed structural analysis of the residues involved in forming the HLA class I binding pockets, one of ordinary skill in the art is enabled to make predictions of sequence motifs for binding to any of the HLA class I proteins.

Using these sequence motifs as search, evaluation, or design criteria, one of ordinary skill in the art is enabled to identify classes of peptides (functional variants of the MAGE-A12 HLA binding peptides disclosed herein) which have a reasonable likelihood of binding to a particular HLA molecule and of interacting with a T cell receptor to induce T cell response. These peptides can be synthesized and tested for activity as described herein. Use of these motifs, as opposed to pure sequence homology (which excludes many peptides which are antigenically similar but quite distinct in sequence) or sequence homology with unlimited "conservative" substitutions (which admits many peptides which differ at critical highly conserved sites), represents a method by which one of ordinary skill in the art can evaluate peptides for potential application in the treatment of disease.

The Strominger and Wucherpfennig PCT application, and references cited therein, all of which are incorporated by reference, describe the HLA class II and TCR binding pockets which contact residues of an HLA class II peptide. Likewise, by keeping the residues which are likely to bind in the HLA class I and/or TCR binding pockets constant or permitting only specified substitutions, functional variants of the MAGE-A12 HLA binding peptides can be prepared which retain binding to HLA class I and T cell receptor.

Localization of one or more antigenic peptides in a protein sequence can be aided by HLA peptide binding predictions made according to established rules for binding potential (e.g., Parker et al, *J. Immunol.* 152:163, 1994; Rammensee et al., *Immunogenetics* 41:178–228, 1995). HLA binding predictions can conveniently be made using an algorithm available via the Internet on the National Institutes of Health World Wide Web site at URL http://bimas.dcrt.nih.gov.

Thus methods for identifying functional variants of a MAGE-A12 immunogenic polypeptide are provided. In general, the methods include selecting a MAGE-A12 HLA binding peptide, an HLA class I binding molecule which binds the MAGE-A12 HLA binding peptide, and a T cell which is stimulated by the MAGE-A12 HLA binding peptide presented by the HLA class I binding molecule. In preferred embodiments, the MAGE-A12 immunogenic polypeptide comprises the amino acid sequence of SEQ ID NO:6. More preferably, the peptide consists of the amino acid sequence of SEQ ID NO:4, SEQ ID NO:5, or SEQ ID NO:6. A first amino acid residue of the MAGE-A12 HLA binding peptide is mutated to prepare a variant peptide. The amino acid residue can be mutated according to the principles of HLA and T cell receptor contact points set forth above. Any method for preparing variant peptides can be employed, such as synthesis of the variant peptide, recombinantly producing the variant peptide using a mutated nucleic acid molecule, and the like.

The binding of the variant peptide to HLA class I binding molecule and/or stimulation of the T cell are then determined according to standard procedures. For example, as exemplified below, the variant peptide can be contacted with an antigen presenting cell which contains the HLA class I molecule which binds the MAGE-A12 HLA binding peptide to form a complex of the variant peptide and antigen presenting cell. This complex can then be contacted with a T cell which recognizes the MAGE-A12 HLA binding peptide presented by the HLA class I binding molecule. T cells can be obtained from a patient having a condition characterized by expression of MAGE-A12. Recognition of variant peptides by the T cells can be determined by measuring an indicator of T cell stimulation such as TNF or IFNγ production.

Binding of the variant peptide to the HLA class I binding molecule and/or stimulation of the T cell by the variant peptide presented by the HLA class I binding molecule indicates that the variant peptide is a functional variant. The methods also can include the step of comparing the stimulation of the T cell by the MAGE-A12 HLA binding peptide and the stimulation of the T cell by the functional variant as a determination of the effectiveness of the stimulation of the T cell by the functional variant. By comparing the functional variant with the MAGE-A12 HLA binding peptide, peptides with increased T cell stimulatory properties can be prepared.

Variants of the MAGE-A12 HLA binding peptides prepared by any of the foregoing methods can be sequenced, if necessary, to determine the amino acid sequence and thus deduce the nucleotide sequence which encodes such variants.

Thus those nucleic acid sequences which code for a MAGE-A12 immunogenic to polypeptide or variant thereof, including allelic variants, are also a part of the invention. In screening for nucleic acids which encode a MAGE-A12 immunogenic polypeptide, a nucleic acid hybridization such as a Southern blot or a Northern blot may be performed under stringent conditions, together with a $^{32}$p probe. The term "stringent conditions" as used herein refers to parameters with which the art is familiar. Nucleic acid hybridization parameters may be found in references which compile such methods, e.g. Molecular Cloning: *A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary stringent conditions include hybridization at 65° C. in hybridization buffer (3.5×SSC, 0.02% Ficoll, 0.02% Polyvinyl pyrolidone, 0.02% Bovine Serum Albumin, 25 mM NaH$_2$PO$_4$ (pH7), 0.5% SDS, 2 mM EDTA). SSC is 0.15M Sodium Chloride/0.015M Sodium Citrate, pH 7; SDS is Sodium Dodecyl Sulphate; and EDTA is Ethylene diaminetetraacetic acid. After hybridization, the membrane upon which the DNA is transferred can be washed, for example, at 2×SSC at room temperature and then at 0.1–0.5×SSC/0.1×SDS at temperatures up to 68° C. After washing the membrane to which DNA encoding a MAGE-A12 immunogenic polypeptide was finally transferred, the membrane can be placed against X-ray film to detect the radioactive signal.

There are other conditions, reagents, and so forth which can used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of nucleic acids encoding the MAGE-A12 immunogenic polypeptides of the invention. The skilled artisan also is familiar with the methodology for screening cells and libraries for expression of such molecules which then are routinely isolated, followed by isolation of the pertinent nucleic acid molecule and sequencing.

The invention also includes the use of nucleic acid sequences which include alternative codons that encode the same amino acid residues of the MAGE-A12 immunogenic polypeptides. For example, as disclosed herein, the peptide VRIGHLYIL (SEQ ID NO:4) is a MAGE-A12 HLA binding peptide. The leucine residues can be encoded by the codons CUA, CUC, CUG, CUU, UUA and UUG. Each of the six codons is equivalent for the purposes of encoding a leucine residue. Thus, it will be apparent to one of ordinary skill in the art that any of the leucine-encoding nucleotide triplets may be employed to direct the protein synthesis apparatus, in vitro or in vivo, to incorporate a leucine residue. Similarly, nucleotide sequence triplets which encode other amino acid residues comprising the MAGE-A12 HLA binding peptide of SEQ ID NO:4 include: GUA, GUC, GUG and GUU (valine codons); GGU, GGA, GGG, GGC (glycine codons); UAC and UAU (tyrosine codons). Other amino acid residues may be encoded similarly by multiple nucleotide sequences. Thus, the invention embraces degenerate nucleic acids that differ from the native MAGE-A12 immunogenic polypeptide encoding nucleic acids in codon sequence due to the degeneracy of the genetic code.

Preferred nucleic acids encoding MAGE-A12 polypeptides are those which preferentially express MAGE-A12 immunogenic polypeptides, such as the HLA binding peptide described herein. The MAGE-A12 nucleic acids of the invention do not encode the entire MAGE-A12 polypeptide but do include nucleotide sequences encoding the MAGE-A12 HLA binding peptide.

The invention also provides modified nucleic acid molecules which include additions, substitutions and deletions of one or more nucleotides. In preferred embodiments, these modified nucleic acid molecules and/or the polypeptides they encode retain at least one activity or function of the unmodified nucleic acid molecule and/or the polypeptides, such as antigenicity, enzymatic activity, receptor binding, formation of complexes by binding of peptides by MHC class I and class [molecules, etc. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules which encode polypeptides having single amino acid changes can be prepared (e.g., preferably not those amino acids which are contact points for HLA binding). Each of these nucleic acid molecules can have one, two or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2–6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

It will also be understood that the invention embraces the use of the sequences in expression vectors, as well as to transfect host cells and cell lines, be these prokaryotic (e.g., E. coli), or eukaryotic (e.g., dendritic cells, CHO cells, COS cells, yeast expression systems and recombinant baculovirus expression in insect cells). The expression vectors require that the pertinent sequence, i.e., those described supra, be operably linked to a promoter. In addition, as it has been found that human HLA-Cw*07 molecules present a MAGE-A12 HLA class I binding peptide, the expression vector may also include a nucleic acid sequence coding for an HLA-Cw*07 molecule. (For other class I or class II binding peptides, different HLA molecules can be used.) In a situation where the vector contains both coding sequences, it can be used to transfect a cell which does not normally express either one. The MAGE-A12 HLA class I binding peptide coding sequence may be used alone, when, e.g. the host cell already expresses an HLA-Cw*07 molecule. Of course, there is no limit on the particular host cell which can be used as the vectors which contain the two coding sequences may be used in host cells which do not express HLA-Cw*07 molecules if desired, and the nucleic acid coding for the MAGE-A12 HLA class I binding peptide can be used in antigen presenting cells which express an HLA-Cw*07 molecule. As used herein, "an HLA-Cw*07 molecule" includes the subtypes HLA-Cw*0701 (07011, 07012), 0702, 0703, 0704, 0705, 0706, 0707, 0708, 0709, 0710, 0711, 0712, 0713 and 0714. An HLA-Cw*07 molecule also includes the subtypes which can be found in Bodmer et al., Tissue Antigens 49:297, 1996. A listing of presently identified HLA-Cw*07 subtypes can be found on the IMGT/HLA database at internet URL http://www.ebi.ac.uk/imgt/hla/.

It will also be understood that the invention embraces the use of the sequences in expression vectors including recombinant plasmids, phagemids, viruses and the like, as well as to transfect host cells and cell lines, be these prokaryotic (e.g., E. coli), or eukaryotic (e.g., dendritic cells, CHO cells, COS cells, yeast expression systems and recombinant baculovirus expression in insect cells). The expression vectors require that the pertinent sequence, i.e., those described supra, be operably linked to a promoter. Delivery of expression vectors containing the MAGE-A12 sequences in vivo and/or in vitro can be via the use of nucleic acid delivery systems known in the art (see, e.g., Allsopp et al., Eur. J. Immunol. 26(8):1951–1959, 1996). Recombinant vectors including viruses selected from the group consisting of adenoviruses, adeno-associated viruses, poxviruses including vaccinia viruses and attenuated poxviruses such as NYVAC, Semliki Forest virus, Venezuelan equine encephalitis virus, retroviruses, Sindbis virus, and Ty virus-like particle, plasmids (e.g. "naked" DNA), bacteria (e.g. the bacterium Bacille Calmette Guerin, BCG), and the like can be used in such delivery, for example, for use as a vaccine. Other viruses, expression vectors and the like which are useful in preparation of a vaccine are known to one of ordinary skill in the art. One can test the MAGE-A12 delivery systems in standard model systems such as mice to determine efficacy of the delivery system. The systems also can be tested in human clinical trials.

In addition, non-MAGE-A12 tumor associated peptides also can be administered to increase immune response via HLA class I and/or class II. It is well established that cancer cells can express more that one tumor associated gene. It is within the scope of routine experimentation for one of ordinary skill in the art to determine whether a particular subject expresses additional tumor associated genes, and then include HLA class I and/or HLA class II binding peptides derived from expression products of such genes in MAGE-A12 compositions and vaccines.

Especially preferred are nucleic acids encoding a series of epitopes, known as "polytopes". The epitopes can be arranged in sequential or overlapping fashion (see, e.g., Thomson et al., Proc. Nail. Acad. Sci. USA 92:5845–5849, 1995; Gilbert et al., Nature Biotechnol. 15:1280–1284, 1997), with or without the natural flanking sequences, and can be separated by unrelated linker sequences if desired. The polytope is processed to generated individual epitopes which are recognized by the immune system for generation of immune responses.

Thus, for example, MAGE-A12 HLA binding peptides such as SEQ ID NOs:4, 5 and 6, and which are presented by MHC molecules and recognized by CTLs (or T helper lymphocytes) can be combined with peptides from other tumor rejection antigens (e.g. by preparation of hybrid nucleic acids or polypeptides) to form "polytopes". Exemplary tumor associated peptide antigens that can be administered to induce or enhance an immune response are derived from tumor associated genes and encoded proteins including MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, GAGE-1, GAGE-2, GAGE-3, GAGE-4, GAGE-5, GAGE-6, GAGE-7, GAGE-8, GAGE-9, BAGE-1, RAGE-1, LB33/MUM-1, PRAME, NAG, MAGE-Xp2 (MAGE-B2), MAGE-Xp3 (MAGE-B3), MAGE-Xp4 (MAGE-B4), tyrosinase, brain glycogen phosphorylase, Melan-A, MAGE-C1, MAGE-C2, MAGE-C3, MAGE-C4, MAGE-C5, NY-ESO-1, LAGE-1, SSX-1, SSX-2 (HOM-MEL-40), SSX-1, SSX-4, SSX-5, SCP-1 and CT-7. For example, antigenic peptides characteristic of tumors include those listed in Table I below.

TABLE I

Exemplary Antigens

| Gene | MHC | Peptide | Position | SEQ ID NO: |
|---|---|---|---|---|
| MAGE-A1 | HLA-A1 | EADPTGHSY | 161–169 | 9 |
|  | HLA-Cw16 | SAYGEPRKL | 230–238 | 10 |
| MAGE-A3 | HLA-A1 | EVDPIGHLY | 168–176 | 11 |
|  | HLA-A2 | FLWGPRALV | 271–279 | 12 |
|  | HLA-B44 | MEVDPIGHLY | 167–176 | 13 |
| BAGE | HLA-Cw16 | AARAVFLAL | 2–10 | 14 |
| GAGE-1, 2 | HLA-Cw16 | YRPRPRRY | 9–16 | 15 |
| RAGE | HLA-B7 | SPSSNRIRNT | 11–20 | 16 |
| GnT-V | HLA-A2 | VLPDVFIRC(V) | 2–10/11 | 17, 18 |
| MUM-1 | HLA-B44 | EEKLIVVLF | exon 2/ intron | 19 |
|  |  | EEKLSVVLF (wild type) |  | 20 |
| CDK4 | HLA-A2 | ACDPHSGHFV | 23–32 | 21 |
|  |  | ARDPHSGHFV (wild type) |  | 22 |
| β-catenin | HLA-A24 | SYLDSGIHF | 29–37 | 23 |
|  |  | SYLDSGIHS (wild type) |  | 24 |
| Tyrosinase | HLA-A2 | MLLAVLYCL | 1–9 | 25 |
|  | HLA-A2 | YMNGTMSQV | 369–377 | 26 |
|  | HLA-A2 | YMDGTMSQV | 369–377 | 42 |
|  | HLA-A24 | AFLPWHRLF | 206–214 | 27 |
|  | HLA-B44 | SEIWRDIDF | 192–200 | 28 |
|  | HLA-B44 | YEIWRDIDF | 192–200 | 29 |
|  | HLA-DR4 | QNILLSNAPLGPQFP | 56–70 | 30 |
|  | HLA-DR4 | DYSYLQDSDPDSFQD | 448–462 | 31 |

TABLE I-continued

Exemplary Antigens

| Gene | MHC | Peptide | Position | SEQ ID NO: |
|---|---|---|---|---|
| Melan-A<sup>MART-1</sup> | HLA-A2 | (E)AAGIGILTV | 26/ 27–35 | 32, 33 |
|  | HLA-A2 | ILTVILGVL | 32–40 | 34 |
| gp100<sup>Pmel117</sup> | HLA-A2 | KTWGQYWQV | 154–162 | 35 |
|  | HLA-A2 | ITDQVPFSV | 209–217 | 36 |
|  | HLA-A2 | YLEPGPVTA | 280–288 | 37 |
|  | HLA-A2 | LLDGTATLRL | 457–466 | 38 |
|  | HLA-A2 | VLYRYGSFSV | 476–485 | 39 |
| PRAME | HLA-A24 | LYVDSLFFL | 301–309 | 40 |
| MAGE-A6 | HLA-Cw16 | KISGGPRISYPL | 292–303 | 41 |
| NY-ESO-1 | HLA-A2 | SLLMWITQCFL | 157–167 | 43 |
|  | HLA-A2 | SLLMWITQC | 157–165 | 44 |
|  | HLA-A2 | QLSLLMWIT | 155–163 | 45 |

Other examples of HLA class I and HLA class II binding peptides will be known to one of ordinary skill in the art (for example, see Coulie, *Stem Cells* 13:393–403, 1995), and can be used in the invention in a like manner as those disclosed herein. One of ordinary skill in the art can prepare polypeptides comprising one or more MAGE-A12 peptides and one or more of the foregoing tumor rejection peptides, or nucleic acids encoding such polypeptides, according to standard procedures of molecular biology.

Thus polytopes are groups of two or more potentially immunogenic or immune response stimulating peptides which can be joined together in various arrangements (e.g. concatenated, overlapping). The polytope (or nucleic acid encoding the polytope) can be administered in a standard immunization protocol, e.g. to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., *Proc. Natl. Acad. Sci USA* 92(13): 5845–5849, 1995; Gilbert et al., *Nature Biotechnol.* 15(12): 1280–1284, 1997; Thomson et al., *J. Immunol.* 157(2): 822–826, 1996; Tam et al., *J. Exp. Med.* 171(1):299–306, 1990). For example, Tam showed that polytopes consisting of both MHC class I and class II binding epitopes successfully generated antibody and protective immunity in a mouse model. Tam also demonstrated that polytopes comprising "strings" of epitopes are processed to yield individual epitopes which are presented by MHC molecules and recognized by CTLs. Thus polytopes containing various numbers and combinations of epitopes can be prepared and tested for recognition by CTLs and for efficacy in increasing an immune response.

It is known that tumors express a set of tumor antigens, of which only certain subsets may be expressed in the tumor of any given patient. Polytopes can be prepared which correspond to the different combination of epitopes representing the subset of tumor rejection antigens expressed in a particular patient. Polytopes also can be prepared to reflect a broader spectrum of tumor rejection antigens known to be expressed by a tumor type. Polytopes can be introduced to a patient in need of such treatment as polypeptide structures, or via the use of nucleic acid delivery systems known in the art (see, e.g., Allsopp et al., *Eur. J. Immunol.* 26(8): 1951–1959, 1996). Adenovirus, pox virus, Ty-virus like particles, adeno-associated virus, plasmids, bacteria, etc. can be used in such delivery. One can test the polytope delivery systems in mouse models to determine efficacy of the delivery system. The systems also can be tested in human clinical trials.

As it has been found that human HLA-Cw*07 molecules present a MAGE-A12 immunogenic polypeptide, the expression vector may also include a nucleic acid sequence coding for an HLA-Cw*07 molecule. Nucleic acids encoding single chain soluble HLA/peptide complex including a MAGE-A12 immunogenic polypeptide fused to an HLA-Cw*07 molecule can be prepared as described by Lone et al. (*J. Immunother.* 21:283–294, 1998).

In a situation where the vector contains both coding sequences, it can be used to transfect a cell which does not normally express either one. The MAGE-A12 immunogenic polypeptide coding sequence may be used alone, when, e.g. the host cell already expresses an HLA-Cw*07 molecule. Of course, there is no limit on the particular host cell which can be used as the vectors which contain the two coding sequences may be used in host cells which do not express HLA-Cw*07 molecules if desired, and the nucleic acid coding for the MAGE-A12 immunogenic polypeptide can be used in antigen presenting cells which express an HLA-Cw*07 molecule.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids, bacteria and virus genomes as disclosed herein, such as adenovirus, poxvirus and BCG. A cloning vector is one which is able to replicate in a host cell or be replicated after its integration into the genome of a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide. As noted above, certain preferred nucleic acids express only fragments of MAGE-A12 polypeptides which include the HLA binding peptides described herein.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a MAGE-A12 immunogenic polypeptide. That heterologous DNA (RNA) is placed under operable control of transcriptional elements to permit the expression of the heterologous DNA in the host cell.

Preferred systems for mRNA expression in mammalian cells are those such as pcDNA3.1 (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992). The use of the adenovirus to express proteins for immunization is disclosed by Warnier et al., in intradermal injection in mice for immunization against PIA (*Int. J. Cancer,* 67:303–310, 1996).

The invention also embraces so-called expression kits, which allow the artisan to prepare a desired expression vector or vectors. Such expression kits include at least separate portions of at least two of the previously discussed materials. Other components may be added, as desired.

The invention as described herein has a number of uses, some of which are described herein. First, the invention permits the artisan to diagnose a disorder characterized by expression of a MAGE-A12 immunogenic polypeptide. These methods involve determining expression of a MAGE-A12 HLA binding peptide, or a complex of a MAGE-A12 HLA binding peptide and an HLA class I molecule in a biological sample. The expression of a peptide or complex of peptide and HLA class I molecule can be determined by assaying with a binding partner for the peptide or complex, such as an antibody. The expression of MAGE-A12 in a biological sample, such as a tumor biopsy, can also be tested by standard PCR amplification protocols using MAGE-A12 primers. An example of tumor expression is presented herein and further disclosure of exemplary conditions and primers for MAGE-A12 amplification can be found in U.S. Ser. No. 09/018,422.

Preferably, the diagnostic methods involve contacting a biological sample isolated from a subject with an agent specific for the MAGE-A12 HLA binding peptide to detect the presence of the MAGE-A12 HLA binding peptide in the biological sample. As used herein, "contacting" means placing the biological sample in sufficient proximity to the agent and under the appropriate conditions of, e.g., concentration, temperature, time, ionic strength, to allow the specific interaction between the agent and MAGE-A12 HLA binding peptide that are present in the biological sample. In general, the conditions for contacting the agent with the biological sample are conditions known by those of ordinary skill in the art to facilitate a specific interaction between a molecule and its cognate (e.g., a protein and its receptor cognate, an antibody and its protein antigen cognate, a nucleic acid and its complementary sequence cognate) in a biological sample. Exemplary conditions for facilitating a specific interaction between a molecule and its cognate are described in U.S. Pat. No. 5,108,921, issued to Low et al.

The biological sample can be located in vivo or in vitro. For example, the biological sample can be a tissue in vivo and the agent specific for the MAGE-A12 immunogenic polypeptide can be used to detect the presence of such molecules in the tissue. Alternatively, the biological sample can be located in vitro (e.g., a blood sample, tumor biopsy, tissue extract). In a particularly preferred embodiment, the biological sample can be a cell-containing sample, more preferably a sample containing tumor cells.

The invention further includes nucleic acid or protein microarrays which include MAGE-A12 HLA binding peptides or nucleic acids encoding such peptides. In this aspect of the invention, standard techniques of microarray technology are utilized to assess expression of the MAGE-A12 HLA binding peptides and/or identify biological constituents that bind such peptides. The constituents of biological samples include antibodies, HLA molecules, lymphocytes (particularly T lymphocytes), and the like. Microarray technology, which is also known by other names including: protein chip technology and solid-phase protein array technology, is well known to those of ordinary skill in the art and is based on, but not limited to, obtaining an array of identified peptides or proteins on a fixed substrate, binding target molecules or biological constituents to the peptides, and evaluating such binding. See, e.g., G. MacBeath and S. L. Schreiber, "Printing Proteins as Microarrays for High-Throughput Function Determination," *Science* 289(5485): 1760–1763, 2000. Nucleic acid arrays, particularly arrays of aptamers that bind MAGE-A12 HLA binding peptides also can be used for diagnostic applications, such as for identifying subjects that have a condition characterized by MAGE-A12 HLA binding peptide expression.

Microarray substrates include but are not limited to glass, silica, aluminosilicates, borosilicates, metal oxides such as alumina and nickel oxide, various clays, nitrocellulose, or nylon. The microarray substrates may be coated with a compound to enhance synthesis of a probe (peptide or nucleic acid) on the substrate. Coupling agents or groups on the substrate can be used to covalently link the first nucleotide or amino acid to the substrate. A variety of coupling agents or groups are known to those of skill in the art. Peptide or nucleic acid probes thus can be synthesized directly on the substrate in a predetermined grid. Alternatively, peptide or nucleic acid probes can be spotted on the substrate, and in such cases the substrate may be coated with a compound to enhance binding of the probe to the substrate. In these embodiments, presynthesized probes are applied to the substrate in a precise, predetermined volume and grid pattern, preferably utilizing a computer-controlled robot to apply probe to the substrate in a contact-printing manner or in a non-contact manner such as ink jet or piezo-electric delivery. Probes may be covalently linked to the substrate.

In some embodiments, one or more control peptide or nucleic acid molecules are attached to the substrate. Preferably, control nucleic acid molecules allow determination of factors such as binding characteristics, reagent quality and effectiveness, hybridization success, and analysis thresholds and success.

The invention also permits the artisan to treat a subject having a disorder characterized by expression of a MAGE-A12 immunogenic polypeptide. Treatments include administering an agent which enriches in the subject a complex of a MAGE-A 12 HLA binding peptide and an HLA class I molecule, and administering CD8+ T lymphocytes which are specific for such complexes. Agents useful in the foregoing treatments include MAGE-A12 immunogenic polypeptides and functional variants thereof, complexes of such peptides and HLA class I binding molecules (e.g. HLA Cw*07), antigen presenting cells bearing complexes of a MAGE-A12 immunogenic polypeptide and an HLA class I binding molecule, soluble single chain fusions of HLA and MAGE-A12 polypeptides, and the like. The invention also permits an artisan to selectively enrich a population of T lymphocytes for CD8+ T lymphocytes specific for a MAGE-A12 HLA binding peptide.

The isolation of the MAGE-A12 HLA binding peptides also makes it possible to isolate or design nucleic acids which encode the MAGE-A12 HLA binding peptides. Nucleic acids can be used to produce in vitro or in prokaryotic or eukaryotic host cells the MAGE-A12 HLA binding peptides or proteins containing such peptides. A variety of methodologies well-known to the skilled practitioner can be utilized to obtain isolated MAGE-A12 HLA binding peptides. For example, an expression vector may be introduced into cells to cause production of the peptides. In another method, mRNA transcripts may be microinjected or otherwise introduced into cells to cause production of the encoded peptides. Translation of mRNA in cell-free extracts such as the reticulocyte lysate system also may be used to produce peptides. Peptides comprising the MAGE-A12 HLA binding peptides of the invention may also be synthesized in vitro. Those skilled in the art also can readily follow known methods for isolating peptides in order to obtain isolated MAGE-A12 HLA binding peptides. These include, but are not limited to, immunochromotography, HPLC, size-exclusion chromatography, ion-exchange chromatography and immune-affinity chromatography.

These isolated MAGE-A12 HLA binding peptides, or complexes of the peptides and HLA class I molecules, such as an HLA-Cw*0701 molecule, may be combined with materials such as adjuvants to produce vaccines useful in treating disorders characterized by expression of the MAGE-A12 immunogenic polypeptide. In addition, vaccines can be prepared from cells which present the MAGE-A12 HLA binding peptide/HLA complexes on their surface, such as transfected dendritic cells, transfected B cells, non-proliferative transfectants, etcetera. In all cases where cells are used as a vaccine, these can be cells transfected with coding sequences for one or both of the components necessary to stimulate CD8+ lymphocytes, or be cells which already express both molecules without the need for transfection. Vaccines also encompass expression vectors and naked DNA or RNA, encoding a MAGE-A12 HLA binding peptide, precursors thereof, or fusion proteins thereof, which may be produced in vitro and administered via injection, particle bombardment, nasal aspiration and other methods. Vaccines of the "naked nucleic acid" type have been demonstrated to provoke an immunological response including generation of CTLs specific for the peptide encoded by the naked nucleic acid (*Science* 259:1745–1748, 1993).

The MAGE-A12 HLA binding peptides, as well as complexes of MAGE-A12 HLA binding peptides and HLA molecules, also may be used to produce antibodies, using standard techniques well known to the art. Standard reference works setting forth the general principles of antibody production include Catty, D., *Antibodies. A Practical Approach*, Vol. 1, IRL Press, Washington D.C. (1988); Klein, J., *Immunology: The Science of Cell-Non-Cell Discrimination*, John Wiley and Sons, New York (1982); Kennett, R., et al., *Monoclonal Antibodies, Hybridoma, A New Dimension In Biological Analyses*, Plenum Press, New York (1980); Campbell, A., *Monoclonal Antibody Technology*, in *Laboratory Techniques and Biochemistry and Molecular Biology*, Vol. 13 (Burdon, R. et al. EDS.), Elsevier Amsterdam (1984); and Eisen, H. N.,*Microbiology*, third edition, Davis, B. D. et al. EDS. (Harper & Rowe, Philadelphia (1980).

The antibodies of the present invention thus are prepared by any of a variety of methods, including administering protein, fragments of protein, cells expressing the protein or fragments thereof and an appropriate HLA class I molecule, and the like to an animal to induce polyclonal antibodies. The production of monoclonal antibodies is according to techniques well known in the art.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of nonspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762 and 5,859, 205.

Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies and human monoclonal antibodies, such as those produced by mice having functional human immunoglobulin gene loci.

Such antibodies may be used for example to identify tissues expressing protein or to purify protein. Antibodies also may be coupled to specific labeling agents for imaging or to antitumor agents, including, but not limited to, methotrexate, radioiodinated compounds, toxins such as ricin, other cytostatic or cytolytic drugs, and so forth, for therapeutic purposes. Antibodies prepared according to the invention also preferably are specific for the peptide/HLA complexes described herein.

When "disorder" or "condition" is used herein, it refers to any pathological condition where the MAGE-A12 immunogenic polypeptide is expressed. Such disorders include cancers, including bladder carcinomas, melanomas, esophageal carcinomas, lung carcinomas, head and neck carcinomas, breast carcinomas, colorectal carcinomas, myelomas, brain tumors, sarcomas, prostate carcinomas and renal carcinomas.

Some therapeutic approaches based upon the disclosure are premised on inducing a response by a subject's immune system to MAGE-A12 immunogenic polypeptide presenting cells. One such approach is the administration of autologous CD8$^+$ T cells specific to the complex of a MAGE-A12 HLA binding peptide and an HLA class I molecule to a subject with abnormal cells of the phenotype at issue. It is within the skill of the artisan to develop such CD8$^+$ T cells in vitro. Generally, a sample of cells taken from a subject, such as blood cells, are contacted with a cell presenting the complex and capable of provoking CD8$^+$ T lymphocytes to proliferate. The target cell can be a transfectant, such as a transfected COS cell, or a transfected antigen presenting cell bearing HLA class I molecules, such as dendritic cells or B cells. These transfectants present the desired complex of their surface and, when combined with a CD8$^+$ T lymphocyte of interest, stimulate its proliferation. COS cells, are widely available, as are other suitable host cells. The clonally expanded autologous CD8$^{30}$ T lymphocytes then are administered to the subject. The CD8$^+$ T lymphocytes then stimulate the subject's immune response, thereby achieving the desired therapeutic goal.

Another method for selecting antigen-specific CTL clones has recently been described (Altman et al., *Science* 274:94–96, 1996; Dunbar et al., *Curr. Biol.* 8:413–416, 1998), in which fluorogenic tetramers of MHC class I molecule/peptide complexes are used to detect specific CTL clones. Briefly, soluble MHC class I molecules are folded in vitro in the presence of $\beta_2$-microglobulin and a peptide antigen which binds the class I molecule. After purification, the MHC/peptide complex is purified and labeled with biotin. Tetramers are formed by mixing the biotinylated peptide-MHC complex with labeled avidin (e.g. phycoerythrin) at a molar ratio or 4:1. Tetramers are then contacted with a source of CTLs such as peripheral blood or lymph node. The tetramers bind CTLs which recognize the peptide antigen/MHC class I complex. Cells bound by the tetramers can be sorted by fluorescence activated cell sorting to isolate the reactive CTLs. The isolated CTLs then can be expanded in vitro for use as described herein.

To detail a therapeutic methodology, referred to as adoptive transfer (Greenberg, J. *Immunol.* 136(5): 1917, 1986; Riddel et al., *Science* 257: 238, 1992; Lynch et al, *Eur. J. Immunol.* 21: 1403–1410, 1991; Kast et al., *Cell* 59: 603–614, 1989), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the relevant HLA/TRA complex. This can be determined very easily, as the art is very familiar with methods for identifying cells which present a particular HLA molecule, as well as how to identify cells expressing DNA of the pertinent sequences, in this case a tumor associated gene sequence. Once cells presenting the relevant complex are identified via the foregoing screening methodology, they can be combined with a sample from a patient, where the sample contains CTLs. If the complex presenting cells are lysed by the mixed CTL sample, then it can be assumed that a tumor associated gene derived TRA is being presented, and the subject is an appropriate candidate for the therapeutic approaches set forth supra.

Adoptive transfer is not the only form of therapy that is available in accordance with the invention. CD8+ T lymphocytes can also be provoked in vivo, using a number of approaches. One approach is the use of non-proliferative cells expressing the complex. The cells used in this approach may be those that normally express the complex, which could be dendritic cells or cells transfected with one or both of the genes necessary for presentation of the complex. Chen et al., (*Proc. Natl. Acad. Sci. USA* 88: 110–114, 1991) exemplifies this approach, showing the use of transfected cells expressing HPV-E7 peptides in a therapeutic regime. Various cell types may be used. Similarly, vectors carrying one or both of the genes of interest may be used. Viral or bacterial vectors are especially preferred. For example, nucleic acids which encode a MAGE-A12 HLA binding peptide may be operably linked to promoter and enhancer sequences which direct expression of the MAGE-A12 HLA binding peptide in certain tissues or cell types. The nucleic acid may be incorporated into an expression vector. Expression vectors may be unmodified extrachromosomal nucleic acids, plasmids or viral genomes constructed or modified to enable insertion of exogenous nucleic acids, such as those encoding MAGE-A12 HLA binding peptides. Nucleic acids encoding a MAGE-A 12 HLA binding peptide also may be inserted into a retroviral genome, thereby facilitating integration of the nucleic acid into the genome of the target tissue or cell type. In these systems, the gene of interest is carried by a microorganism, e.g., a Vaccinia virus, retrovirus or the bacteria BCG, and the materials de facto "infect" host cells. The cells which result present the complex of interest, and are recognized by autologous CD8+ T cells, which then proliferate.

A similar effect can be achieved by combining a MAGE-A12 HLA binding peptide with an adjuvant to facilitate incorporation into HLA class I presenting cells in vivo. If larger than the HLA class I binding portion, the MAGE-A12 HLA binding peptide can be processed if necessary to yield the peptide partner of the HLA molecule while the TRA is presented without the need for further processing. Generally, subjects can receive an intradermal injection of an effective amount of the MAGE-A12 immunogenic polypeptide. Initial doses can be followed by booster doses, following immunization protocols standard in the art.

As part of certain immunization compositions, one or more cancer associated antigens or stimulatory fragments thereof are administered with one or more adjuvants to induce an immune response or to increase an immune response. An adjuvant is a substance incorporated into or administered with antigen which potentiates the immune response. Adjuvants may enhance the immunological response by providing a reservoir of antigen (extracellularly or within macrophages), activating macrophages and stimulating specific sets of lymphocytes. Adjuvants of many kinds are well known in the art. Specific examples of adjuvants include monophosphoryl lipid A (MPL, SmithKline Beecham), a congener obtained after purification and acid hydrolysis of Salmonella Minnesota Re 595 lipopolysaccharide; saponins including QS21 (SmithKline Beecham), a pure QA-21 saponin purified from *Quillaja saponaria* extract; DQS21, described in PCT application WO96/33739 (SmithKline Beecham); QS-7, QS-17, QS-18, and QS-L1 (So et al., *Mol. Cells* 7:178–186, 1997); incomplete Freund's adjuvant; complete Freund's adjuvant; montanide; immunostimulatory oligonucleotides (see e.g. CpG oligonucleotides described by Kreig et al., *Nature* 374:546–9, 1995); and various water-in-oil emulsions prepared from biodegradable oils such as squalene and/or tocopherol. Preferably, the peptides are administered mixed with a combination of DQS21/MPL. The ratio of DQS21 to MPL typically will be about 1:10 to 10:1, preferably about 1:5 to 5:1 and more preferably about 1:1. Typically for human administration, DQS21 and MPL will be present in a vaccine formulation in the range of about 1 μg to about 100 μg. Other adjuvants are known in the art and can be used in the invention (see, e.g. Goding, *Monoclonal Antibodies: Principles and Practice*, 2nd Ed., 1986). Methods for the preparation of mixtures or emulsions of peptide and adjuvant are well known to those of skill in the art of vaccination.

Other agents which stimulate the immune response of the subject can also be administered to the subject. For example, other cytokines are also useful in vaccination protocols as a result of their lymphocyte regulatory properties. Many other cytokines useful for such purposes will be known to one of ordinary skill in the art, including interleukin-12 (IL-12) which has been shown to enhance the protective effects of vaccines (see, e.g., *Science* 268: 1432–1434, 1995), GM-CSF and IL-18. Thus cytokines can be administered in conjunction with antigens and adjuvants to increase the immune response to the antigens.

There are a number of additional immune response potentiating compounds that can be used in vaccination protocols. These include costimulatory molecules provided in either protein or nucleic acid form. Such costimulatory molecules include the B7-1 and B7-2 (CD80 and CD86 respectively) molecules which are expressed on dendritic cells (DC) and interact with the CD28 molecule expressed on the T cell. This interaction provides costimulation (signal 2) to an antigen/MHC/TCR stimulated (signal 1) T cell, increasing T cell proliferation and effector function. B7 also interacts with CTLA4 (CD152) on T cells and studies involving CTLA4 and B7 ligands indicate that the B7-CTLA4 interaction can enhance antitumor immunity and CTL proliferation (Zheng et al., *Proc. Nat'l Acad. Sci. USA* 95:6284–6289, 1998).

B7 typically is not expressed on tumor cells so they are not efficient antigen presenting cells (APCs) for T cells. Induction of B7 expression would enable the tumor cells to stimulate more efficiently CTL proliferation and effector function. A combination of B7/IL-6/IL-12 costimulation has been shown to induce IFN-gamma and a Th1 cytokine profile in the T cell population leading to further enhanced T cell activity (Gajewski et al., *J. Immunol.* 154:5637–5648, 1995). Tumor cell transfection with B7 has been discussed in relation to in vitro CTL expansion for adoptive transfer immunotherapy by Wang et al. (*J. Immunother.* 19:1–8, 1996). Other delivery mechanisms for the B7 molecule would include nucleic acid (naked DNA) immunization (Kim et al., *Nature Biotechnol.* 15:7:641–646, 1997) and recombinant viruses such as adeno and pox (Wendtner et al., *Gene Ther.* 4:726–735, 1997). These systems are all amenable to the construction and use of expression cassettes for the coexpression of B7 with other molecules of choice such as the antigens or fragment(s) of antigens discussed herein (including polytopes) or cytokines. These delivery systems can be used for induction of the appropriate molecules in vitro and for in vivo vaccination situations. The use of anti-CD28 antibodies to directly stimulate T cells in vitro and in vivo could also be considered. Similarly, the inducible co-stimulatory molecule ICOS which induces T cell responses to foreign antigen could be modulated, for example, by use of anti-ICOS antibodies (Hutloff et al., *Nature* 397:263–266, 1999).

Lymphocyte function associated antigen-3 (LFA-3) is expressed on APCs and some tumor cells and interacts with CD2 expressed on T cells. This interaction induces T cell IL-2 and IFN-gamma production and can thus complement but not substitute, the B7/CD28 costimulatory interaction (Parra et al., *J. Immunol.*, 158:637–642, 1997; Fenton et al., *J Immunother.*, 21:95–108, 1998).

Lymphocyte function associated antigen-1 (LFA-1) is expressed on leukocytes and interacts with ICAM-1 expressed on APCs and some tumor cells. This interaction induces T cell IL-2 and IFN-gamma production and can thus complement but not substitute, the B7/CD28 costimulatory interaction (Fenton et al., 1998). LFA-1 is thus a further example of a costimulatory molecule that could be provided in a vaccination protocol in the various ways discussed above for B7.

Complete CTL activation and effector function requires Th cell help through the interaction between the Th cell CD40L (CD40 ligand) molecule and the CD40 molecule expressed by DCs (Ridge et al., *Nature* 393:474, 1998; Bennett et al., *Nature* 393:478, 1998; Schoenberger et al., *Nature* 393:480, 1998). This mechanism of this costimulatory signal is likely to involve upregulation of B7 and associated IL-6/IL-12 production by the DC (APC). The CD40-CD40L interaction thus complements the signal 1 (antigen/MHC-TCR) and signal 2 (B7-CD28) interactions.

The use of anti-CD40 antibodies to stimulate DC cells directly, would be expected to enhance a response to tumor associated antigens which are normally encountered outside of an inflammatory context or are presented by nonprofessional APCs (tumor cells). In these situations Th help and B7 costimulation signals are not provided. This mechanism might be used in the context of antigen pulsed DC based therapies or in situations where Th epitopes have not been defined within known tumor associated antigen precursors.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents. The term "pharmaceutically acceptable" means a non-toxic material that does not interfere with the effectiveness of the biological activity of the active ingredients. The characteristics of the carrier will depend on the route of administration.

The therapeutics of the invention can be administered by any conventional route, including injection or by gradual infusion over time. The administration may, for example, be oral, intravenous, intraperitoneal, intramuscular, intranasal, intracavity, subcutaneous, intradermal or transdermal.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention also contemplates gene therapy. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy using vectors such as adenovirus also is contemplated according to the invention.

The preparations of the invention are administered in effective amounts. An effective amount is that amount of a pharmaceutical preparation that alone, or together with further doses, stimulates the desired response. In the case of treating cancer, the desired response is inhibiting the progression of the cancer. This may involve only slowing the progression of the disease temporarily, although more preferably, it involves halting the progression of the disease permanently. In the case of inducing an immune response, the desired response is an increase in antibodies or T lymphocytes which are specific for the MAGE-A12 immunogen(s) employed. These desired responses can be monitored by routine methods or can be monitored according to diagnostic methods of the invention discussed herein.

Where it is desired to stimulate an immune response using a therapeutic composition of the invention, this may involve the stimulation of a humoral antibody response resulting in an increase in antibody titer in serum, a clonal expansion of cytotoxic lymphocytes, or some other desirable immunologic response. It is believed that doses of immunogens ranging from one nanogram/kilogram to 100 milligrams/kilogram, depending upon the mode of administration, would be effective. The preferred range is believed to be between 500 nanograms and 500 micrograms per kilogram. The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation.

EXAMPLES

Materials and Methods

Cell Lines

Bladder carcinoma cell line LB831-BLC was derived from the primary invasive bladder tumor (pT3, G3) of a 65-yr-old Caucasian patient, LB831 (HLA-A*2403, -A3, -B*4403, -B*4901, -Cw*0401, -Cw*07). The karyotype of the cell line performed at passage 7 showed that the number of chromosomes varied from 56 to 144, confirming that the LB831 cell line was a tumor line. Mu13443-MEL is a melanoma cell line and LE9211-RCC is a renal carcinoma cell line. Both were derived from an HLA-Cw7-negative patient. LB373-MEL is a melanoma line derived from an HLA-Cw7-negative patient. The tumor cells were cultured in Iscove's medium (Life Technologies, Gaithersburg, Md.) containing 10% human serum or 10% FCS (Life Technologies) in a 8% $CO_2$ incubator. Lymphoblastoid cell line LB-831-EBV was derived from the PBLs of patient LB831 with 1 µg/ml of Cyclosporine A (Sandoz, Basel, Switzerland) and 20% (v/v) of supernatant of EBV transformed B95–8 cells using standard techniques. This cell line was grown in RPMI-1640 medium (Life Technologies)

containing 10% FCS in a 5% $CO_2$ incubator. PBL-PHA cells were prepared by stimulation of PBL with 0.1% (v/v) PHA (Difco) and 100 U/ml of EL-2 (Eurocetus, Amsterdam, Netherlands) and cultured in an 8% $CO_2$ incubator in Iscove's medium containing 10% human serum. All media were supplemented with L-arginine (116 μg/ml), L-asparagine (36 μg/ml), L-glutamine (216 μg/ml), streptomycin (0.1 mg/ml) and penicillin (200 U/ml).

Anti-Tumor CTL Clones

Blood mononuclear cells of patient LB831 were isolated by Lymphoprep (Nycomed, Oslo, Norway) density-gradient centrifugation and stored at −80° C. Autologous mixed lymphocyte-tumor cell culture was performed by mixing irradiated B7-1 transfected LB831-BLC cells as stimulators and CD8+ T lymphocytes as responders as described previously (Guéguen et al., J Immunology 160:6188–6194, 1998). CD8+ T lymphocytes were sorted with magnetic beads covalently coupled to anti-CD8 antibodies (MACS, Miltenyi Biotec GmbH). Irradiated non-CD8+ cells were added to the mixed culture during the first stimulation. On day 3, IL-2 (25 U/ml) was added. After one week, $5 \times 10^5$ lymphocytes were restimulated with irradiated B7-1-transfected tumor cells and 25 U/ml IL-2. On day 28, lymphocytes from the culture were cloned by limiting dilution in Iscove's medium supplemented with IL-2 (50 U/ml). Long-term culture of CTL clones was carried out as described (Herin et al., Int. J. Cancer 39:390–396, 1987).

Cytotoxicity Assay

The lytic activity of CTLs was tested in a chromium release assay as described previously (Boon et al., J. Exp. Med. 152:1184–1193, 1980). Briefly, 1,000 chromium-labeled cells in 100 μl were incubated in 96-well microplates with an equal volume of CTL at different effector to target ratios. Chromium release was measured after 4 h of incubation. For the peptide assay, labeled LB831-EBV cells were incubated for 30 min at 37° C. with various concentrations of peptides. CTL were then added and chromium release was measured as described above.

CTL Stimulation Assay

A total of 3,000 CTLs were added to microwells containing 10,000 stimulator cells in 100 μl of Iscove's medium supplemented with 10% human serum and 25 U/ml of IL-2. After 24 h, the supernatant was collected and its TNF content determined by testing the cytotoxic effect on WEHI-164 clone 13 cells (Espevik and Nissen-Meyer, J. Immunol. Methods 95:99–105, 1986) in an MTT colorimetric assay (Hansen et al., J. Immunol. Meth. 119:203–210, 1989). Inhibition with mAbs W6/32 (anti-HLA class I), B1.23.2 (anti-HLA-B and C), B9.4.1 (anti-CD8), 1B8.2 (anti-CD4, donated by D. Olive, INSERM U119, Marseille, France), GAPA-3 (anti-H LA-A3), C7709A2.6 (anti-HLA-A24) was performed by addition of a 1/20-1/30 dilution of ascites to the test.

Transient Transfections

Transient transfection was performed with the LipofectAMINE™ reagent (Life Technologies). Briefly, $5 \times 10^4$ 293-EBNA cells (293 cells expressing EBV nuclear antigen EBNA-1) were transfected in a flat-bottomed 96-well plate with 100 ng of DNA of the MAGE-A12 cDNA or subgenic fragments cloned into pcDNA3 (Invitrogen, Carlsbad, Calif.), 50 ng of plasmid pcDNA3 containing the HLA-Cw*0701, and 1.5 μl of LipofectAMINE™. LB373-MEL cells (10,000) were transfected with 150 ng of the HLA-Cw7 construct and 1 μl of lipofectAMINE. Transfected cells were tested in a CTL stimulation assay after 24 h.

Cloning of the HLA-Cw7 cDNA from LB831-BLC was performed as described previously (Guéguen et al., 1998). Its sequence was identical to allelic subtype Cw*07011, except at position 1087 of the coding sequence where G was found instead of A. This nucleotide change causes the replacement of a threonine by an alanine in the intracytoplasmic domain of the molecule. The same difference has been described between the Cw*0704 and Cw*0711 alleles (Baurain and Coulie, Tissue Antigens 53:510–512, 1999).

Stable Transfection of Tumor Cell Lines

Bladder cell carcinoma LB831-BLC was transfected by the calcium phosphate precipitation method, as described previously (Traversari et al., Immunogenetics 35:145–152, 1992). $1 \times 10^6$ cells were transfected with 20 μg of plasmid pEF-BOS puro-PL3 containing the cDNA B7-1. Briefly, B7-1 was amplified using sense primer 5'-GGGTCCAAATTGTTGGCTTTCACT (SEQ ID NO:7) and anti-sense primer 5'-GAAGAATGCCTCATGATCCCCA (SEQ ID NO:8) in a PCR reaction with cDNA from cell line LB23-EBV as template. PCR conditions were as described by Gueguen et al., 1998. The B7-1 insert was then cloned into plasmid pEF-BOSpuro-PL3, which was derived from pEF-BOS (Mishizuma and Nagata, Nucleic Acids Res. 18:5322, 1990) by insertion of a puromycin resistance gene and a polylinker. Puromycin-resistant LB831-BLC cells were selected in 0.8 μg/ml puromycin (Sigma, St. Louis, Mo.) and then cloned by limiting dilution.

Cloning of Subgenic Fragments of Gene MAGE-A12

A MAGE-A12 cDNA containing the entire open reading frame (ORF) of 945 bp was used as a template for PCR amplification (DePlaen et al., Immunogenetics 40:360–369, 1994). Eight fragments containing the first 195, 342, 525, 540, 591, 651, 683 and 816 nucleotides of the MAGE-A12 ORF were amplified using the forward primer
5'-CCTACCTGCTGCCCTGACCA-3' (LHE7; SEQ ID NO:46) and reverse primers
5'-CCTAAGGACTGTGGGGAGGA-3' (LHE2; SEQ ID NO:47),
5'-CCAACTAAGCCATCTTCCTA-3' (LHE3; SEQ ID NO:48),
5'-GTGACAAGGATCTACAAGTG-3' (LHE4; SEQ ID NO:49),
5'-CCAGTCAGGTGACAAGGATG-3' (LHE10; SEQ ID NO:50),
5'-CCTGTCTAGGGCACGATCTG-3' (LHE8; SEQ ID NO:51),
5'-CTCCTAAGGGGCACAGTCGC-3' (LHE9; SEQ ID NO:52),
5'-TCAGATGCCTACAACACACT-3'(LHE5; SEQ ID NO:53), and
5'-GGACCCTACAGGAACTCGTA-3' (LHE6; SEQ ID NO:54), respectively. Taq DNA polymerase (TaKaRa Taq) was used for PCR amplification. A first denaturation step was performed for 5 min at 94° C., and then 25 cycles of amplification were performed as follows: 1 min at 94° C. for all primers, 2 min at 62° C. for primers LHE3, LHE4 and LHE5 or 2 min at 64° C. for primers LHE2, LHE6, LHE8, LHE9, and LHE 10; and 3 min at 72° C. for all primers. Cycling was concluded with a final elongation step of 10 min at 72° C. The PCR products were cloned into pcDNA3 vector using the Bidirectional Eukaryotic TOPO TA Cloning Kit (Invitrogen).

PCR Assay for MAGE-A12 Expression

RT-PCR was performed to detect the expression of MAGE-A12 in tumor tissues. Total RNA purification and cDNA synthesis were conducted as previously described (Weynants et al., Int. J. Cancer 56:826–829, 1994). One fortieth of the cDNA produced from 2 μg of total RNA was amplified using sense primer 5'-CGTTGGAGGTC- AGAGAACAG-3' (SEQ ID NO:55) and anti-sense primer 5'-GCCCTCCACTGATCTTTAGCAA-3' (SEQ ID NO:56). For PCR, a first denaturation step was done for 4 min at 94° C., and then 32 cycles of amplification were performed as follows: 1 min at 94° C., 2 min at 62° C., and 3 min at 72° C. Cycling was concluded with a final extension step of 15 min at 72° C.

Example 1

A New Antigenic Peptide Derived From Gene MAGE-A12 and Recognized by an HLA-Cw*0701 Restricted CTL of a Bladder Carcinoma-Patient LB831-BLC is a bladder carcinoma cell line expressing at least three antigens recognized by autologous CTL; one of them has already been described (Guéguen et al., J Immunology 160:6188–6194, 1998). An autologous mixed lymphocyte tumor-cell culture (MLTC) was performed by mixing irradiated B7-1 transfected LB831-BLC cells cultured in human serum as stimulators and $CD8^+$ T lymphocytes as responders. $CD8^+$ T lymphocytes were sorted with magnetic beads that had been covalently coupled to anti-CD8 Abs (magnetic-activated cell sorter, Milteny Biotec, Bergisch-Gladbach, Germany). Irradiated non-CD8+ cells were added to the mixed culture during the first stimulation. On day 3[L-2 (50 U/ml) was added. After one week $5\times10^5$ lymphocytes were restimulated with irradiated B7-1 transfected tumor cells and 25 U/ml IL-2. On day 28, lymphocytes from the culture were cloned by limiting dilution in Iscove's medium supplemented with IL-2 (50 U/ml). A panel of LB831-specific CTL-clones was obtained, among them CTL 501 D/19 which recognizes the autologous tumor line but not the autologous EBV-transformed B-cells (i.e., it recognizes an antigen distinct from the first three antigens, called LB831-D).

To determine the MHC-restriction of these CTL clones, the inhibitory effect of anti-HLA mAbs on clone stimulation was studied. CTL clone 501D/19 produced TNF when stimulated with LB831-BLC cells, and this production was completely blocked in the presence of anti-HLA class I mAb W6/32 or in the presence of a monoclonal antibody (mAb B1.23.2) directed against a common determinant of HLA-B and —C molecules. As the HLA typing of LB831 is HLA -A*2403, -A*3, -B*4403, -B*4901, -Cw*0401, and -Cw*07, this result indicated that the target antigen is presented either by HLA-B*44, B*49, Cw*04 or Cw*07.

Additional target cells were recognized by CTL 501D/19 in a standard 4 h chromium release assay. As shown in FIG. 1A, CTL 501D/19 also lysed two allogeneic tumor lines, melanoma line MI113443-MEL and renal carcinoma line LE9211-RCC. The targets were: LB831-BLC (the autologous bladder carcinoma line); LB831-EBV (autologous EBV-transformed B cells); LE9211-RCC (an allogeneic HLA-Cw4 and HLA-Cw7-positive renal carcinoma line); M113443-MEL (an allogeneic HLA-Cw4 and HLA-Cw7-positive melanoma line); and K562 (natural killer target). The allogeneic and the autologous tumor lines were pretreated with IFNγ for 1 or 5 days, respectively, before being used as targets. Chromium release was measured after 4 h.

All of the foregoing tumor cells are negative for B*44 and B*49, but positive for Cw*04 and Cw*07. To confirm which HLA presented the tumor antigen, melanoma cell lines were transiently transfected with Cw*04 or Cw*07 and tested for recognition by CTL 501 D/19. Only the Cw*07 transfectants were recognized by CTL. As shown in FIG. 1B, LB373-MEL (a melanoma cell line derived from an HLA-Cw7-negative patient) was transiently transfected with an HLA-Cw7 plasmid construct. Three thousand CTLs were added to 10,000 stimulator cells, and the production of TNF by the CTLs was measured after 24 hr. As CTL 501D/19 also recognizes HLA-Cw*07-positive melanoma line NaMel6 it was concluded that antigen LB831-D is presented by the HLA-Cw*07 molecule. The allelic subtype of the Cw*07 gene of LB83]-BLC was determined and found to be HLA-Cw*07011.

Figure 2:
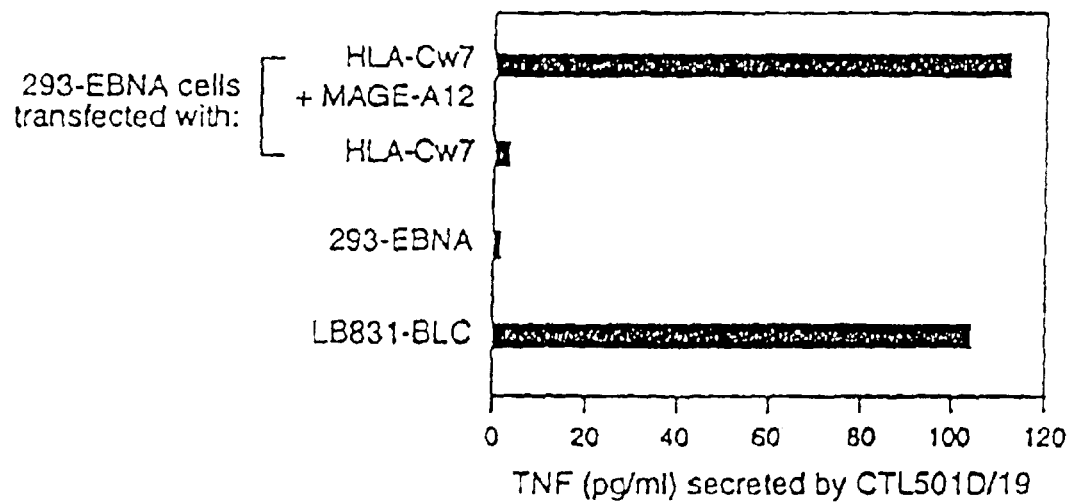
FIG. 2 shows that CTL 501D/19 recognizes an antigen encoded by MAGE-12 and presented by HLA-Cw7.

To determine whether the LB831-D antigen recognized by CTL 501 D/19 was encoded by an already known gene, 293-EBNA cells were cotransfected with expression vectors containing the HLA-Cw*0701 cDNA and with a series of genes including, among others, the MAGE, BAGE, GAGE, RAGE, $LAGE^{NY-ESO1}$ cDNAs which were found to be expressed at a high level in the bladder tumor sample of patient LB831. The transfectants were tested for their ability to stimulate TNF production by CTL 501 D/19. Twenty four hours after transfection, the cells were incubated with 3000 cells of CTL 501D/19. After 24 hours, the amount of TNF in the supernatant was measured by assessing its cytotoxicity for WEHI-164–13 cells. LB831-BLC cells were used as positive control. TNF was only produced by the CTL when stimulated with 293-EBNA cells transfected with HLA-Cw*07 and gene MAGE-A12 (FIG. 2). No stimulation was observed with 293-EBNA cells transfected with HLA-Cw7 alone or with the combination of HLA-Cw7 and any other gene.

By RT-PCR it was ascertained that all of the tumor lines that were recognized by CTL 501D/19 expressed MAGE-A12, confirming that the antigen is encoded by this gene. Other HLA-Cw7 restricted CTL clones generated in the MLTC were also examined. Six additional CTL clones were found that recognized 293-EBNA cells transfected with MAGE-A12 and HLA-Cw7.

Figure 3:
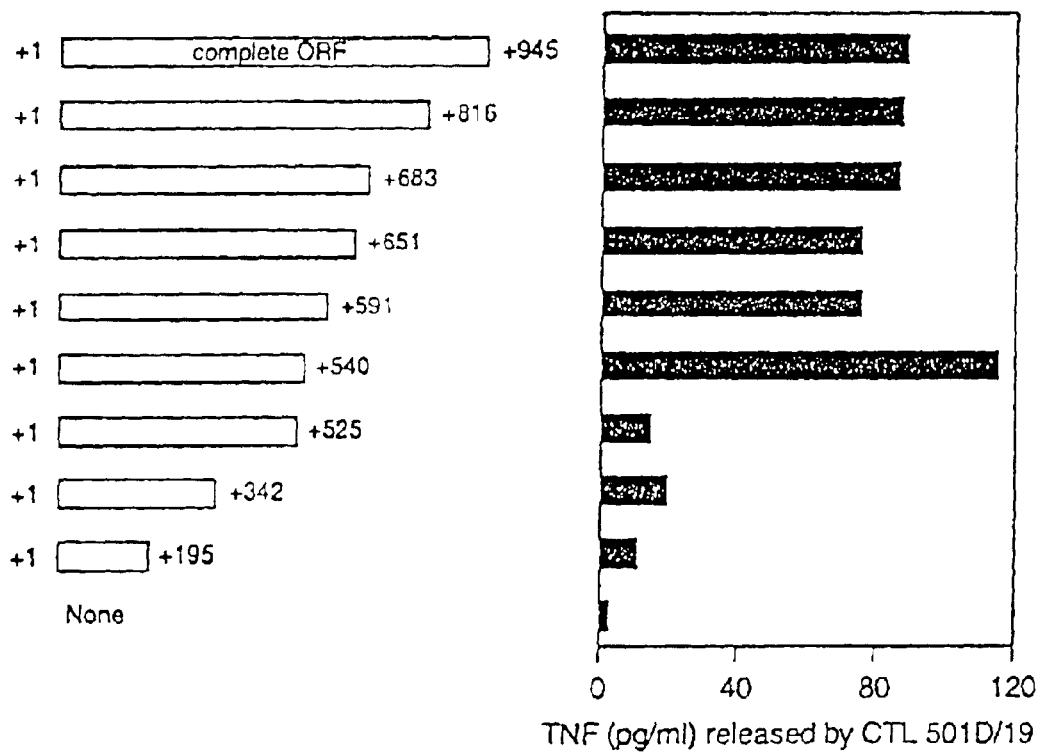
FIG. 3 shows the identification of the MAGE-A12 region coding for the antigenic peptide recognized by CTL 501D/19.

To identify the MAGE-A12 sequence that codes for the antigenic peptide, MAGE-A12 fragments of different lengths were generated by PCR. These subgenic fragments were cloned into pcDNA3 and transfected into 293-EBNA cells together with the HLA-Cw*0701 construct. A CTL stimulation assay was conducted with the transfectants (FIG. 3). Transfected cells were incubated for 24 h with CTL 501D/19, and the TNF production in the supernatants was measured by its toxicity to WEHI-164.13 cells. The numbering of the PCR fragments corresponds to the nucleotides of the coding region.

Figure 4:
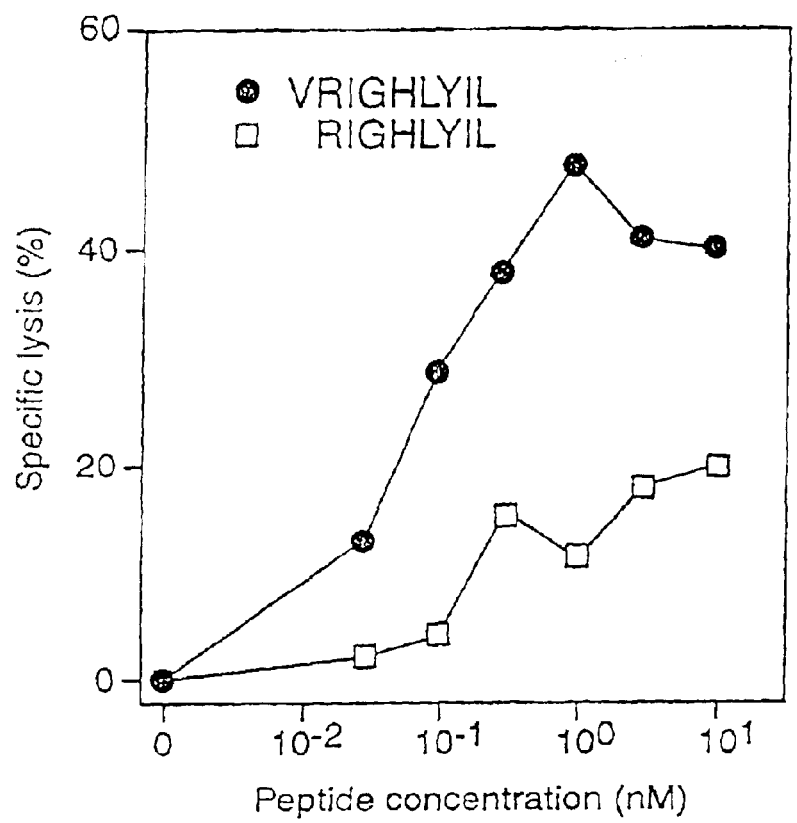
FIG. 4 depicts lysis by CTL 501D/19 of the autologous cell line LB-831-EBV pulsed with MAGE-12 peptides VRIGHLYIL (SEQ ID NO:4) and RIGHLYIL (SEQ ID NO:6).

Cells transfected with fragments of 540 bp or more were capable of stimulating CTL 501D/19, whereas those transfected with shorter fragments were not. This indicated that the end of the sequence coding for the antigenic peptide was located between nucleotide 525 and 540 of the MAGE-A12 ORF. In the amino-acid sequence corresponding to nucleotides 525–540, two overlapping nonapeptides, EVVRIGHLY (codons 168–176 of MAGE-A12; SEQ ID NO:3) and VRIGHLYIL (codons 170–178 of MAGE-A12; SEQ ID NO:4) were found which conformed to the HLA-Cw7 peptide binding motif, i.e. tyrosine or leucine at the C terminus (Rammensee et al., Immunogenetics. 41:178, 1995). Decapeptide VVRIGHLYL (SEQ ID NO:5), nonapeptide VRIGHLYIL (SEQ ID NO:4) and octapeptide RIGHLYIL (SEQ ID NO:6) sensitized the autologous lymphoblastoid cell line LB-83]-EBV to lysis by CTL 501D/19 (FIG. 4). Autologous cell line LB-831-EBV was loaded with MAGE-A12 peptides VRIGHLYIL (SEQ ID NO:4), VVRIGHLYIL (SEQ ID NO:5), or RIGHLYIL (SEQ ID NO:6), and contacted with CTL 501D/19. Chromium-labeled cells were pulsed for 30 min with the indicated concentrations of peptides (VRIGHLYIL (SEQ ID NO:4) or RIGHLYL (SEQ ID NO:6)). CTL 501D/19 was added at an effector to target ratio of 10. Chromium release was measured after 4 hours. Peptides lacking the C-terminal leucine (e.g., EVVRIGHLY, SEQ ID NO:3) were also tested and were not recognized. Half-maximal lysis was obtained with a remarkably low concentration of nonapeptide VRIGHLYIL (SEQ ID NO:4), 100 pM, indicating that this peptide is recognized very efficiently by CTL 501D/19.

Example 2

Expression of MAGE-A12 in Tumor Samples

Expression of MAGE-A12 was determined in tumor samples and/or cell lines of a variety of tumors by RT-PCR. The PCR amplifications were carried out using MAGE-A12 specific primers and conditions as described above. The results of the MAGE-A12 RT-PCR amplifications are provided in Table I.

| Sample type | Number of samples tested | MAGE-A12 positive samples n | % |
|---|---|---|---|
| Melanoma, cutaneous | | | |
| primaries | 83 | 28 | 34 |
| metastases | 243 | 151 | 62 |
| | 326 | 179 | 55 |
| Esophageal | | | |
| squamous-cell carcinoma | 19 | 5 | 26 |
| adenocarcinoma | 5 | 2 | 40 |
| | 24 | 7 | 29 |
| Lung | | | |
| squamous-cell carcinoma | 93 | 26 | 28 |
| adenocarcinoma | 43 | 14 | 33 |
| | 136 | 40 | 29 |
| Head and Neck | | | |
| squamous-cell carcinoma | 85 | 23 | 27 |
| Bladder carcinoma | | | |
| superficial (<T2) | 70 | 7 | 10 |
| infiltrating (≧T2) | 53 | 18 | 34 |
| | 123 | 25 | 20 |
| Breast carcinoma | 50 | 8 | 16 |
| Colorectal carcinoma | 46 | 5 | 11 |
| Myeloma | | | |
| stage I–II | 11 | 0 | 0 |
| stage III | 27 | 4 | 15 |
| | 38 | 4 | 11 |
| Brain tumors | 11 | 1 | 9 |
| Sarcomas | 13 | 1 | 8 |
| Prostate gland adenocarcinoma | 22 | 1 | 5 |
| Renal carcinoma | 6 | 0 | 0 |
| Uterine tumors | 5 | 0 | 0 |
| Thyroid tumors | 4 | 0 | 0 |
| Pleural mesothelioma | 4 | 0 | 0 |
| Leukemia | 112 | 0 | 0 |

Equivalents

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

---

We claim:

1. An isolated MAGE-A12 HLA class I binding peptide consisting of a fragment of the amino acid sequence of SEQ ID NO:2 which binds HLA Cw*07, wherein the fragment comprises an amino acid sequence selected from the group consisting of SEQ ID NO:4, SEQ ID NO:5, and SEQ ID NO:6.

2. A composition comprising the isolated MAGE-A12 HLA class I binding peptide of claim 1 and a pharmaceutically acceptable carrier.

3. A non-hydrolyzable isolated MAGE-A12 HLA class I-binding peptide consisting of a fragment of the amino acid sequence of SEQ ID NO: 2 that binds HLA Cw*07, wherein the fragment comprises an amino acid sequence selected from the group consisting of SEQ ID NO: 4, SEQ ID NO: 5 and SEQ ID NO: 6, wherein said sequence comprises one or more D-amino acid residues.

4. A non-hydrolyzable isolated MAGE-A12 HLA class I-binding peptide consisting of a fragment of the amino acid sequence of SEQ ID NO: 2 that binds HLA Cw*07, wherein the fragment comprises an amino acid sequence selected from the group consisting of SEQ ID NO: 4, SEQ ID NO: 5 and SEQ ID NO: 6, wherein said sequence comprises one or more non-hydrolyzable peptide bonds selected from the group consisting of a -psi[CH$_2$NH]-reduced amide peptide bond, a -psi[COCH$_2$]-ketomethylene peptide bond, a -psi [CH(CN)NH]-(cyanomethylene)amino peptide bond, a -psi [CH$_2$CH(OH)]-hydroxyethylene peptide bond, a -psi [CH$_2$O]-peptide bond, and a -psi[CH$_2$S]-thiomethylene peptide bond.

5. An isolated MAGE-A12 HLA-C binding peptide consisting of the amino acid sequence of SEQ ID NO:4.

6. A composition comprising the isolated MAGE-A12 HLA class I binding peptide of claim 5 and a pharmaceutically acceptable carrier.

7. A non-hydrolyzable isolated MAGE-A12 HLA-C binding peptide consisting of the amino acid sequence of SEQ ID NO: 4, wherein said sequence comprises one or more D-amino acid residues.

8. A non-hydrolyzable isolated MAGE-A12 HLA-C binding peptide consisting of the amino acid sequence of SEQ ID NO: 4, wherein said sequence comprises one or more non-hydrolyzable peptide bonds selected from the group consisting of a -psi[CH$_2$NH]-reduced amide peptide bond, a -psi[COCH$_2$]-ketomethylene peptide bond, a -psi[CH(CN) NH]-cyanomethylene)amino peptide bond, a -psi[CH$_2$CH (OH)]-hydroxyethylene peptide bond, a -psi[CH$_2$O]-peptide bond, and a -psi[CH$_2$S]-thiomethylene peptide bond.

9. An isolated MAGE-A12 HLA-C binding peptide consisting of the amino acid sequence of SEQ ID NO:5.

10. A composition comprising the isolated MAGE-A12 HLA class I binding peptide of claim 9 and a pharmaceutically acceptable carrier.

11. A non-hydrolyzable isolated MAGE-A12 HLA-C binding peptide consisting of the amino acid sequence of SEQ ID NO: 5, wherein said sequence comprises one or more D-amino acid residues.

12. A non-hydrolyzable isolated MAGE-A12 HLA-C binding peptide consisting of the amino acid sequence of SEQ ID NO: 5, wherein said sequence comprises one or more non-hydrolyzable peptide bonds selected from the group consisting of a -psi[$CH_2NH$]-reduced amide peptide bond, a -psi[$COCH_2$]-ketomethylene peptide bond, a -psi[CH(CN)NH]-(cyanomethylene)amino peptide bond, a -psi[$CH_2CH(OH)$]-hydroxyethylene peptide bond, a -psi[$CH_2O$]-peptide bond, and a -psi[$CH_2S$]-thiomethylene peptide bond.

13. An isolated MAGE-A12 HLA class I-binding peptide consisting of the amino acid sequence of SEQ ID NO:6.

14. A composition comprising the isolated MAGE-A12 HLA class I binding peptide of claim 13 and a pharmaceutically acceptable carrier.

15. A non-hydrolyzable isolated MAGE-A12 HLA class I-binding peptide consisting of the amino acid sequence of SEQ ID NO: 6, wherein said sequence comprises one or more D-amino acid residues.

16. A non-hydrolyzable isolated MAGE-A12 HLA class I-binding peptide consisting of the amino acid sequence of SEQ ID NO: 6, wherein said sequence comprises one or more non-hydrolyzable peptide bonds selected from the group consisting of a -psi[$CH_2NH$]-reduced amide peptide bond, a -psi[$COCH_2$]-ketomethylene peptide bond, a -psi[CH(CN)NH]-(cyanomethylene)amino peptide bond, a -psi[$CH_2CH(OH)$]-hydroxyethylene peptide bond, a -psi[$CH_2O$]-peptide bond, and a -psi[$CH_2S$]-thiomethylene peptide bond.

\* \* \* \* \*

UNITED STATES PATENT AND TRADEMARK OFFICE
CERTIFICATE OF CORRECTION

PATENT NO. : 6,897,288 B1
DATED : May 24, 2005
INVENTOR(S) : Heidecker et al.

It is certified that error appears in the above-identified patent and that said Letters Patent is hereby corrected as shown below:

Column 54,
Line 43, delete "peptidc" and replace with -- peptide --.

Signed and Sealed this

Nineteenth Day of July, 2005

JON W. DUDAS
*Director of the United States Patent and Trademark Office*